US012594100B2

(12) United States Patent
Powers et al.

(10) Patent No.: US 12,594,100 B2
(45) Date of Patent: Apr. 7, 2026

(54) OSTEOTOMY DEVICE AND METHODS

(71) Applicant: OrthoPediatrics Corp., Warsaw, IN (US)

(72) Inventors: Chris Powers, Warsaw, IN (US); Sarah Poorman, Columbia City, IN (US); Luis Vega, Warsaw, IN (US); Cristian Gurrola, Fort Wayne, IN (US); Grace Gibbs, Warsaw, IN (US)

(73) Assignee: OrthoPediatrics Corp., Warsaw, IN (US)

( * ) Notice: Subject to any disclaimer, the term of this patent is extended or adjusted under 35 U.S.C. 154(b) by 558 days.

(21) Appl. No.: 17/679,504

(22) Filed: Feb. 24, 2022

(65) Prior Publication Data

US 2022/0395304 A1     Dec. 15, 2022

Related U.S. Application Data

(62) Division of application No. 16/225,689, filed on Dec. 19, 2018, now Pat. No. 11,266,449.

(60) Provisional application No. 62/607,580, filed on Dec. 19, 2017.

(51) Int. Cl.
| | |
|---|---|
| *A61B 17/80* | (2006.01) |
| *A61B 17/16* | (2006.01) |
| *A61B 17/88* | (2006.01) |
| *A61B 17/00* | (2006.01) |
| *A61B 17/56* | (2006.01) |
| *A61B 17/68* | (2006.01) |
| *A61B 90/00* | (2016.01) |

(52) U.S. Cl.
CPC ...... *A61B 17/8019* (2013.01); *A61B 17/1604* (2013.01); *A61B 17/8095* (2013.01); *A61B 17/885* (2013.01); *A61B 17/8866* (2013.01); *A61B 2017/00407* (2013.01); *A61B 2017/564* (2013.01); *A61B 2017/681* (2013.01); *A61B 2090/061* (2016.02)

(58) Field of Classification Search
CPC .. A61F 2/44; A61F 2/447; A61F 2/442; A61F 2/46; A61F 2/30; A61F 2/30771; A61F 2/80; A61F 2/88; A61F 2/8866; A61F 2/8095
See application file for complete search history.

(56) References Cited

U.S. PATENT DOCUMENTS

| | | | | |
|---|---|---|---|---|
| 2009/0076516 A1* | 3/2009 | Lowry | .................. | A61B 17/02 606/90 |
| 2013/0053854 A1* | 2/2013 | Schoenefeld | .......... | A61B 34/10 606/87 |
| 2014/0163563 A1* | 6/2014 | Reynolds | ........... | A61B 17/1717 606/86 R |

* cited by examiner

*Primary Examiner* — Christopher J Beccia
(74) *Attorney, Agent, or Firm* — Gerald W. Roberts; John V. Daniluck; Dentons Bingham Greenebaum LLP

(57) ABSTRACT

Methods and apparatus for performing an osteotomy. One embodiment includes a kit comprising a bone plate, a bridging device, and a spreading device. The bridge is configured to hold open the incision in the bone, whether the spreading device is inserted into the bone, or the bone plate is attached to the bone. The spreading device preferably includes a scissors-type mechanism for spreading two wedge-shaped members apart, contemplating both pivotal and displacement movements of one wedging member relative to another wedging member. The spring device preferably includes an ergonomic grip for the hand of the physician, and a hammering surface useful in inserting the spreading device into the incision.

18 Claims, 25 Drawing Sheets

FIG. 12A     FIG. 12B     FIG. 12C

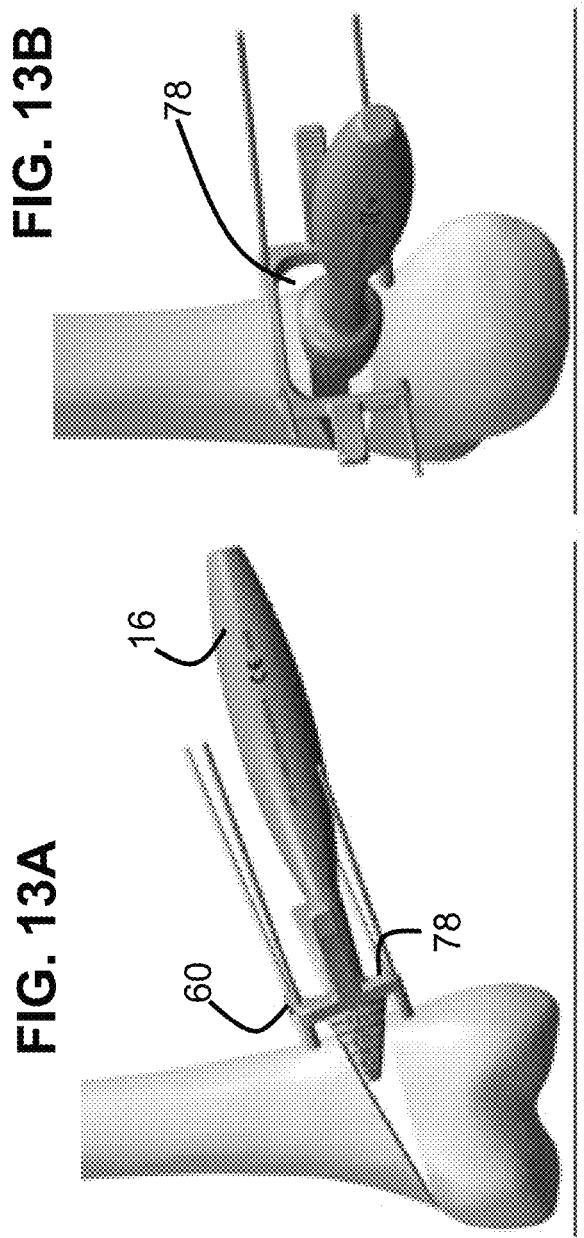
FIG. 13A
FIG. 13B
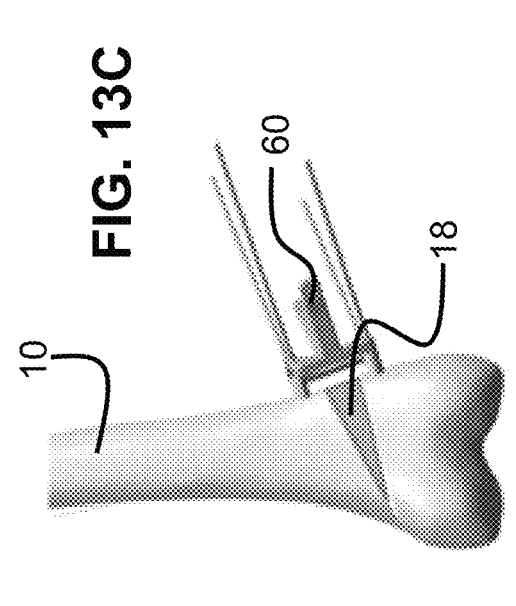
FIG. 13C

OSTEOTOMY DEVICE AND METHODS

CROSS REFERENCE TO RELATED APPLICATION

This application is a divisional of U.S. patent application Ser. No. 16/225,689, filed Dec. 19, 2018, which claims the benefit of priority to U.S. Provisional Patent Application Ser. No. 62/607,580, filed Dec. 19, 2017, both of which are incorporated herein by reference.

FIELD OF THE INVENTION

Various embodiments of the present invention pertain to devices for spreading apart two surfaces and maintaining the spatial relationship between those two surfaces, and in particular to a spreading device useful in osteotomies and a bridging device useful for securement of the osteotomy during surgery.

SUMMARY OF THE INVENTION

One embodiment of the present invention pertains to a kit for performing a medical procedure, the kit preferably including a spreading device for spreading apart a portion of the anatomy of an animal, a bridge to hold open the anatomy and a bone plate to cover the anatomy.

Yet another embodiment of the present invention pertains to a spreading device with a hand grip that can be conveniently held in the hand of a physician, the device including a hammering region relative to the hand grip which is useful for driving the spreading device into an incision.

Yet another embodiment of the present invention pertains to a spreading device capable of spreading apart from a nested position to an open position, and including a scissors-type actuation mechanism for opening the spreading device.

Yet another embodiment of the present invention pertains to a spreading device that includes two separable members, the device having a wedge shape when the members are fully closed. As the members are spread apart by an internal actuation device, the members can move to, and through, a range of overall shapes, including wedge shape, trapezoidal shape, and any manner of polygonal shape.

Yet another embodiment of the present invention pertains to a bridging device that is adapted and configured to be attached to both sides of an incised area of anatomy of an animal, including a bone being prepared for an osteotomy, the embodiments bridging device includes an open, central volume that can accommodate a spreading device or jacking device located in the incision. In yet other embodiments the bridging device has an open, central volume that provides clearance for the spreading device, in a general shape that provides two posts for connection on either side of the incision (or on different bones).

In still further embodiments, the bridging device is attached to the anatomy surrounding incision such that there is sufficient space provided for a bone plate to be placed across the incision, with at least one fastener holding the bone plate to the bone.

Yet another embodiment of the present invention pertains to a variable angle pin compression/distraction device. In some embodiments, there are wire tubes can be locked into desired orientation or left to rotate freely during use. Still further embodiments allow the user to distract/compress linearly or in an angular fashion, and gives user freedom for trajectory of initial wire insertion.

Yet another embodiment of the present invention pertains to a device for attachment to bones, including a rack & pinion feature can be locked into a specific spacing after adjustment of the location of the rack arm relative to the pinion arm. In some embodiments, the device can function as a bridge to provisionally hold desired correction of osteotomy while final fixation is obtained.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled CAD drawings or from photographs that are scalable. It is understood that such dimensions, or the relative scaling within a figure, are by way of example, and not to be construed as limiting. Persons of ordinary skill will also recognize that CAD renderings may include lines that pertain to changes in surface geometry, and not necessarily to component features.

FIG. 12A shows the bone of FIG. 11B with a bridging device about to be positioned over the spreading member.

FIG. 12B shows the bone of FIG. 12A with the bridging device surrounding the spreading device.

FIG. 12C shows the bridging device being temporarily attached to the bone.

FIG. 13A shows a measurement device measuring the opening of the wedge.

FIG. 13B shows the arrangement of FIG. 13A, and showing the measurement device within the open aperture of the bridging device.

FIG. 13C shows a graft after insertion into the wedge opening.

ELEMENT NUMBERING

Figure 1:
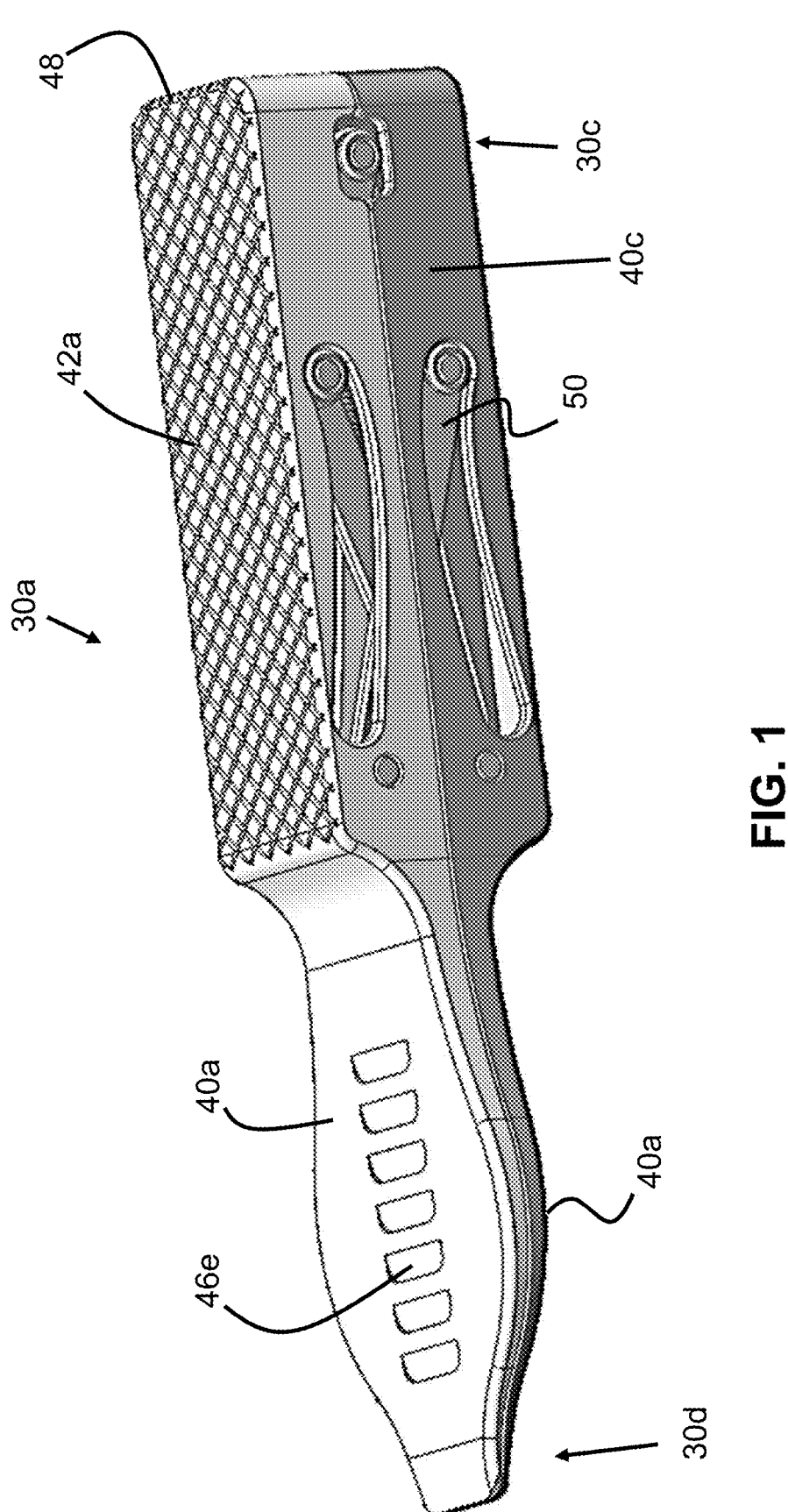
FIG. 1 is a left side, top, frontal perspective scaled CAD representation of a jacking device or spreading device according to one embodiment of the present invention shown in the fully nested or closed position.

The following is a list of element numbers and at least one noun used to describe that element. It is understood that none of the embodiments disclosed herein are limited to these nouns, and these element numbers can further include other words that would be understood by a person of ordinary skill reading and reviewing this disclosure in its entirety.

| | |
|---|---|
| 10 | Bone |
| 11 | cutting guide |
| a | Wire |
| b | Guide |
| 12 | Incision |
| 14 | wedge opening |
| 16 | measurement device |
| 18 | bone graft |
| 20 | guide wires |
| 24 | bone plate |
| a | head width |
| b | heel width |
| 26 | Fasteners |
| 30 | jacking device; spreading device |
| a | fully nested or closed |
| b | opened |
| c | proximal end |
| d | distal end |
| 31 | longitudinal axis |
| 40 | spreading member |
| a | top surface |
| b | inner surface; nesting surface |
| c | lateral surfaces |
| 42 | gripping region |
| a | knurled surface |
| b | maximum exterior width |
| c | cam profile |
| d | collar and pivot relief |
| e | driver access port |
| f | internal nesting volume |
| 46 | bone contact region |
| a | distalmost tip |
| b | maximum bone contact width |
| c | stiffening rib |
| d | receiving pocket |
| e | one-way sliding features |
| 47 | shoulder |
| 48 | hammering end |
| 50 | actuation device means for spreading |
| 51 | central threaded actuator; driving member |
| 52 | scissors mechanism |
| 53 | collars |
| a | outermost |
| b | innermost |
| c | end stop with pin |
| 54 | links |
| a | outer proximal |
| b | inner proximal |
| c | outer distal |
| d | inner distal |
| 56 | pivotal connection |
| a | link to collar |
| b | link to link |
| c | link to member |
| d | cam follower |
| 60 | bridging device |
| 62 | handle |
| 70 | interconnecting wall; peripheral wall |
| 72 | segments |
| a | first |
| b | second |
| c | third |
| 76 | opening |
| 78 | central aperture |
| a | width |
| b | depth |
| 80 | standoff posts |
| a | post |
| b | post |
| c | post |
| d | post |
| 82 | bore |
| 83 | wire guides |
| 84 | bone contact surface |
| 85 | bone plate allowance |

-continued

| | |
|---|---|
| a | head |
| b | heel |
| 86 | clearance height |
| 88 | offsets |
| a | lateral |
| b | longitudinal |
| 90 | adjustable bridging device |
| 91 | adjustable bridging device without collets |
| 92 | rack assembly |
| a | frame; arm |
| b | rack gear |
| c | bone attachment assembly |
| d | pinion guide |
| e | Indicia |
| f | Pocket |
| 94 | pinion assembly |
| a | frame; arm |
| b | pinion gear |
| b1 | rack-engageable teeth |
| b2 | rack-interfering teeth |
| c | bone attachment assembly |
| d | rack receptacle |
| e | retention spring assembly |
| f | knob |
| g | window |
| h | locking teeth |
| 96 | variable angle post assembly |
| a | post |
| b | head |
| c | dimple; recess |
| d | shaft |
| e | inner guide; lumen |
| f | bone contact surface |
| g | threaded interface; ext. locking device |
| h | knob; external. locking device |
| i | projection; ext. locking device |
| 98 | guide wire receptacle; collet |
| a | shaft |
| b | slots; region of reduced hoop stiffness |
| c | threads |
| d | knob |
| e | lumen |

DETAILED DESCRIPTION OF ONE OR MORE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "preferably," refers to features and aspects that are present in at least one embodiment, but which are optional for some embodiments, it therefore being understood that use of the word "preferably" implies the term "optional."

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

This document may use different words to describe the same element number, or to refer to an element number in a specific family of features (NXX.XX). It is understood that such multiple, different words are not intended to provide a redefinition of any language herein. It is understood that such words demonstrate that the particular feature can be considered in various linguistical ways, such ways not necessarily being additive or exclusive.

Various embodiments of the present invention pertain to instruments that assist a surgeon in an osteotomy. In one embodiment, the invention includes a kit of devices, including a spreading or jacking device, a temporary bridge, and a bone plate. In one embodiment, the jacking device and the bone plate are each of a size and geometric configuration that each be present at the same time that the temporary bridging device is attached to the bone, and yet still provide the surgeon with largely unimpeded access to the osteotomy. In yet other embodiments it will be appreciated that the bridging device can perform temporary securement of the osteotomy, and provide access to various different types of spreading devices, bone plates, measurement devices, and other surgical instruments.

In still further embodiments, one embodiment of the invention includes a spreading or jacking device that pivots open into a V-shape, and closes into a compact shape with substantially all of the actuation mechanism being contained between the outer surfaces of the device, and in some embodiments within an interior volume defined by the jacking device. In one embodiment, the device includes a pair of spreading members that, at one end, include surfaces adapted and configured to push against the incised surfaces of the osteotomy. The other end of the members form a housing between which or within which an actuation device resides.

In one embodiment, the actuation device is adapted and configured to spread apart the two members such that the distalmost end located in the osteotomy forms a wedge or V-shape, with the distalmost tips of the members staying in close contact, while the other, proximal end members separate as the open end of the V-shape. It is understood that distal tips stay in close contact in one embodiment, although in other embodiments the distal tips slightly spread apart, while still maintaining a V-shape. In still further embodiments, the tips remain in contact.

In still other embodiments, the spreading members separate in parallel or almost parallel fashion. In yet other embodiments, the two members spread apart in a reverse V-shape, such that the distal ends spread apart more than the proximal ends of the spreading members. However, in still further embodiments, the actuator functions to spread apart the distalmost tips in any kind of motion, including, for example motion in which the tips initially spread apart, and in which subsequent actuation causes the tips to come closer together. It is further understood that various other embodiments of the jacking device shown herein have applicability outside of the surgical world.

In one embodiment, the actuation device is centrally located, and internal to the spatial envelope of the spreading members. Preferably, substantially all of the actuation device remains located between the spreading members as the device is opened and the members spread apart. In this manner, the jacking device establishes and maintains a relatively low space claim proximate to the incision.

In one embodiment, the actuation device is a scissors-type jacking mechanism, similar in some respects to automobile jacks. However, unlike an automobile jack in which the top pair of pivot joints are maintained parallel to the bottom pair of pivot joints in some embodiments of the present invention a top pivot axle and an opposite, bottom pivot axle are both pivotal and slidable within a curving cam and follower groove. By adapting and configuring the pivoting axles to follow the cam groove, the V-shape or wedging opening action is accomplished as the central screw is rotated. However, yet other embodiments of the present invention contemplate any type of spreading mechanism, including, for example ratcheting jacking actuators (similar to automobile bumper jacks, and others).

In some embodiments, the follower groove has a shape that is calculated to provide a variety of geometric relationships between the position of the actuation mechanism, and the distance between the distal ends, and the difference between the proximal ends. It is understood that various embodiments are not limited to simple angular spreading motion, or a fixed combination of angular spreading and lateral displacement. As examples, various embodiments contemplate actuation mechanisms adapted and configured to provide a shape of the spreading device that is triangular, a wedge, a trapezoid, or parallelogram. In some embodiments the actuation mechanism establishes a center of rotation point for one of the members relative to the other member, and can move the relative location of that center of rotation point. To accomplish this, in some embodiments the shape of the cam follower groove is established by curve fitting a variety of variable combinations of angular rotation and lateral displacement as the actuation mechanism traverses from the nested position to the expanded position.

Yet other embodiments of the present invention pertain to a bridging device useful for temporarily maintaining two opposing surfaces separated from one another, while providing a central working area that permits largely unimpeded access to the spread apart surfaces. In one embodiment, the device includes a peripheral wall that extends more than 180 degrees around a central aperture. In yet other embodiments, the peripheral wall extends less than about 270 degrees about a central aperture. The wall includes a plurality of attachment posts that have a length adapted and configured to space apart the wall from the surface of the incised bone. With such a configuration, the bridging device can be placed around the spreading device when the device is opened and spreading apart the surfaces of the incision. Preferably, the bridge includes a pair of handles that extend outward and away from the central aperture, so as to permit ease of handling by the surgeon, yet not impede access to the incision through the central aperture.

In further embodiments, the bridge includes a plurality of standoff posts that are spaced apart to permit a bone plate to be slid underneath the interconnecting wall and placed directly on the bone surface while the bridge is temporarily attached to the bone surface. In some embodiments, esp. those in which the bone plate has a narrower end and a wider end, the posts can be spread apart more widely at one end, and more narrowly at the other end, similar to (but greater than) the corresponding width of the bone plate. Preferably, the bridge is located by the surgeon to straddle the osteotomy while a jacking device is in place and spreading the osteotomy apart. Preferably, a portion of the interconnecting wall between otherwise adjacent posts is removed to further allow the bridge to be slid axially along the bone, with the spreading device being able to pass between the unconnected standoff posts. This "removed" or missing segment of the bridge provides an opening or gap through which the spreading device can pass.

In still further embodiments, the bridging device includes a peripheral wall that extends around a central aperture, the central aperture being adapted and configured to provide substantial, unimpeded access to the widest opening of the wedge gap in the bone. This central aperture has a height (or depth) that is greater than the height (or depth) of the spread apart jacking device at the particular elevation of the peripheral wall relative to the bone surface. Further, the central aperture has a width that is greater than the width of the jacking device when it is in the incision.

FIGS. 1-5 present various views of jacking devices or spreading devices 30 and 130 according to various embodiments of the present invention. Those of ordinary skill in the art will recognize that many of the comments made to describe spreading device 30 apply either specifically or generally to spreading device 130, as will be discussed. These figures are scaled figures from a CAD database sufficiently detailed to support the manufacture of the device.

Figure 2:
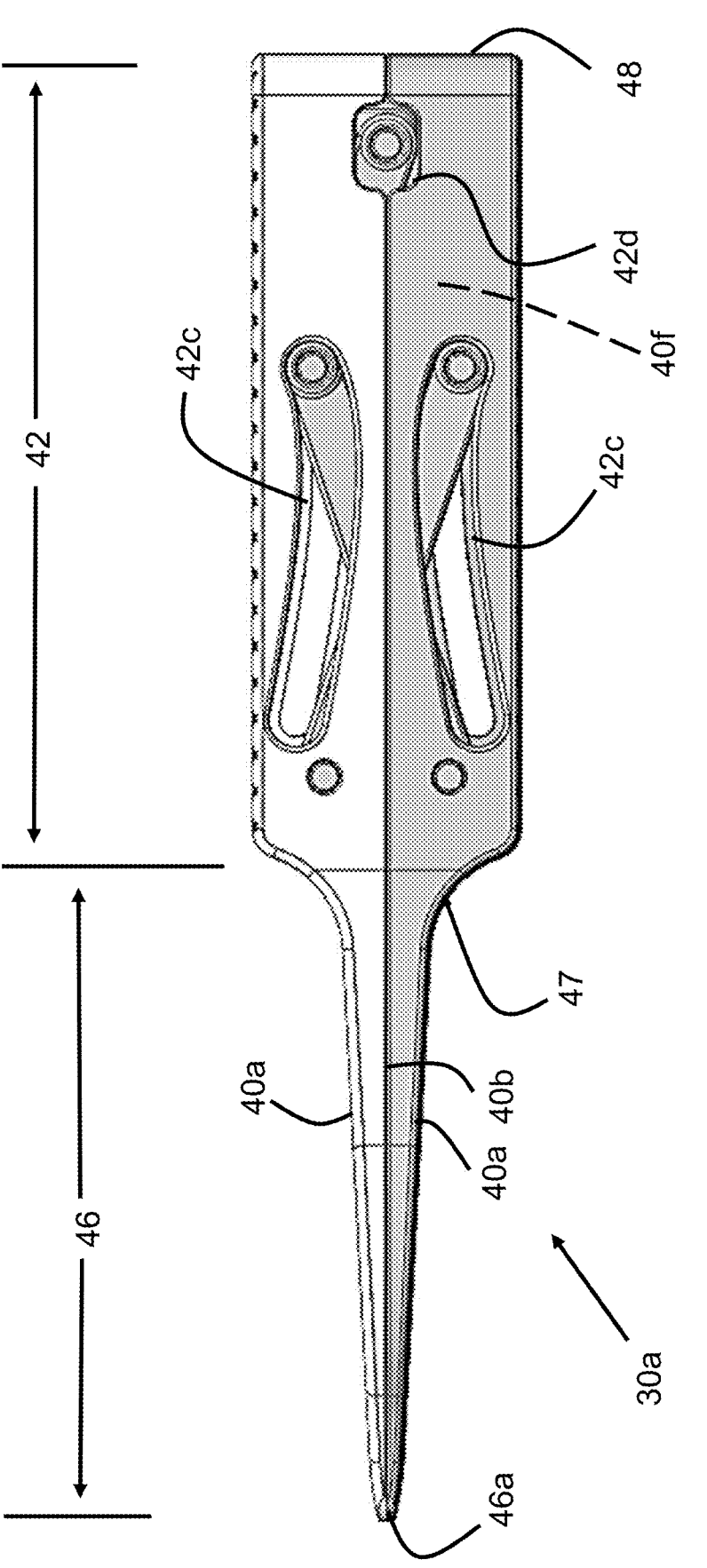
FIG. 2 is a left side elevational view of the apparatus of FIG. 1.

FIGS. 1 and 2 show the device in the 30a fully nested or closed position. Device 30 includes top and bottom spreading members 40 that preferably extend from the distalmost end 46 to the most proximal end 48. As used herein, proximal refers to a closer distance to the surgeon, and distal refers to a closer distance to the opposite end, with the distal end being inserted into the bone.

It can be seen that the top and bottom members 40 are preferably identical to one another, although the present invention also contemplates those embodiments in which the top and bottom members 40 have different shapes or functions. A member 40 includes a gripping region 42 that is adapted and configured to be gripped by the hand of the physician, and a bone contact region 46 that is adapted and configured to penetrate an incision, widen the incision, and be in contact with the tissue of the bone, including the cancellous material of the bone. A preferably rounded shoulder 47 separates the two regions.

Figure 5:
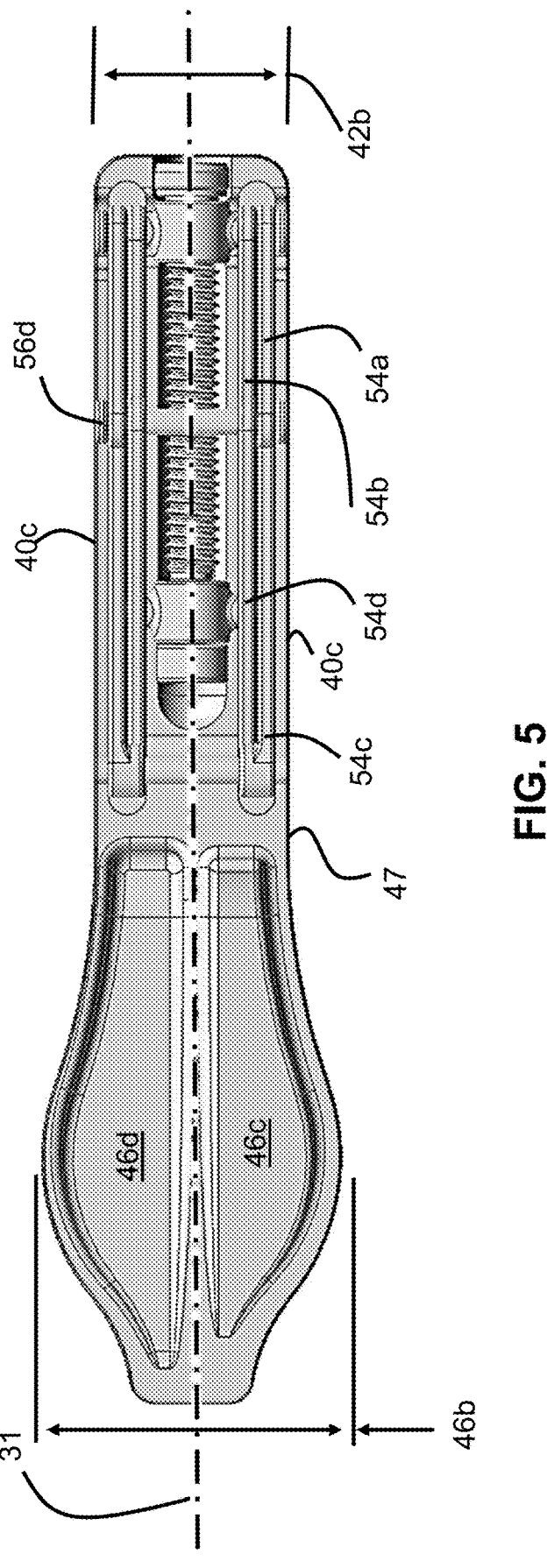
FIG. 5 is a top planar view looking downward of the apparatus of FIG. 4A, with the jacking device shown in the fully closed position.

As best seen in FIG. 5, the planar shape of a spreading member is generally linear in the gripping region, having a maximum exterior width 42b. The bone contact region 46 preferably has a maximum contact width 46b that occurs intermediate of the shoulder 47 and the distal tip 46a. Therefore, as spreading device 30 is inserted into a bone incision, the bone contact region 46 is in contact with a relatively larger surface of the cut bone. However, the present invention also contemplates those embodiments in which the bone contact region is of any shape, and in which the gripping region 42 is of any shape. As one example, in some embodiments the gripping region 42 may be curving or cylindrical, if such shapes are preferred by the surgeon.

As best seen in FIG. 1, gripping region 42 preferably includes surface features 42a, such as a cross-hatched surface to facilitate a secure handhold. Further, the lateral width of the top surface as well as the vertical height of the gripping region are adapted and configured to be within a range of dimensions that facilitate comfortable encirclement by the hand of the surgeon.

FIG. 1 also shows one or more surface features 46e that are adapted and configured to facilitate sliding of the bone contact region 46 into an incision, but to resist unwanted slippage or removal of the spreading member from the incision. In one embodiment, these one-way sliding features 46e each have proximal and distal sides, with the proximal side being slightly raised relative to the distal side, and in one example, the features are rearward-facing ramps. As the contact region is moved into an incision, these features provide relatively little resistance. However, if the bone contact surface 46 is in contact with the bone and is slid in a proximal direction (i.e., being removed from the incision) then the rearward face of these surface features 46e resist removal. Therefore, in various embodiments of the present invention, the spreading device preferably is moved toward the nested position prior to removal. However, yet other embodiments contemplate bone contact regions that are smooth and featureless.

Referring to FIG. 2, it can be seen that the upper and lower spreading members 40 have substantially identical top and bottom shapes, although other embodiments of the present invention contemplate spreading members that have shapes different than the side planar shape shown in FIG. 2, or the top planar view shown in FIG. 5). It can also be seen in FIG. 2 as well as the other figures that each spreading member 40 includes a cam profile 40c, a relief cutout 42d to provide clearance for a collar 53a and pivot joint 56a, as well as a driver access port 42d located on the rear facing, proximalmost face 48.

Figure 4A:
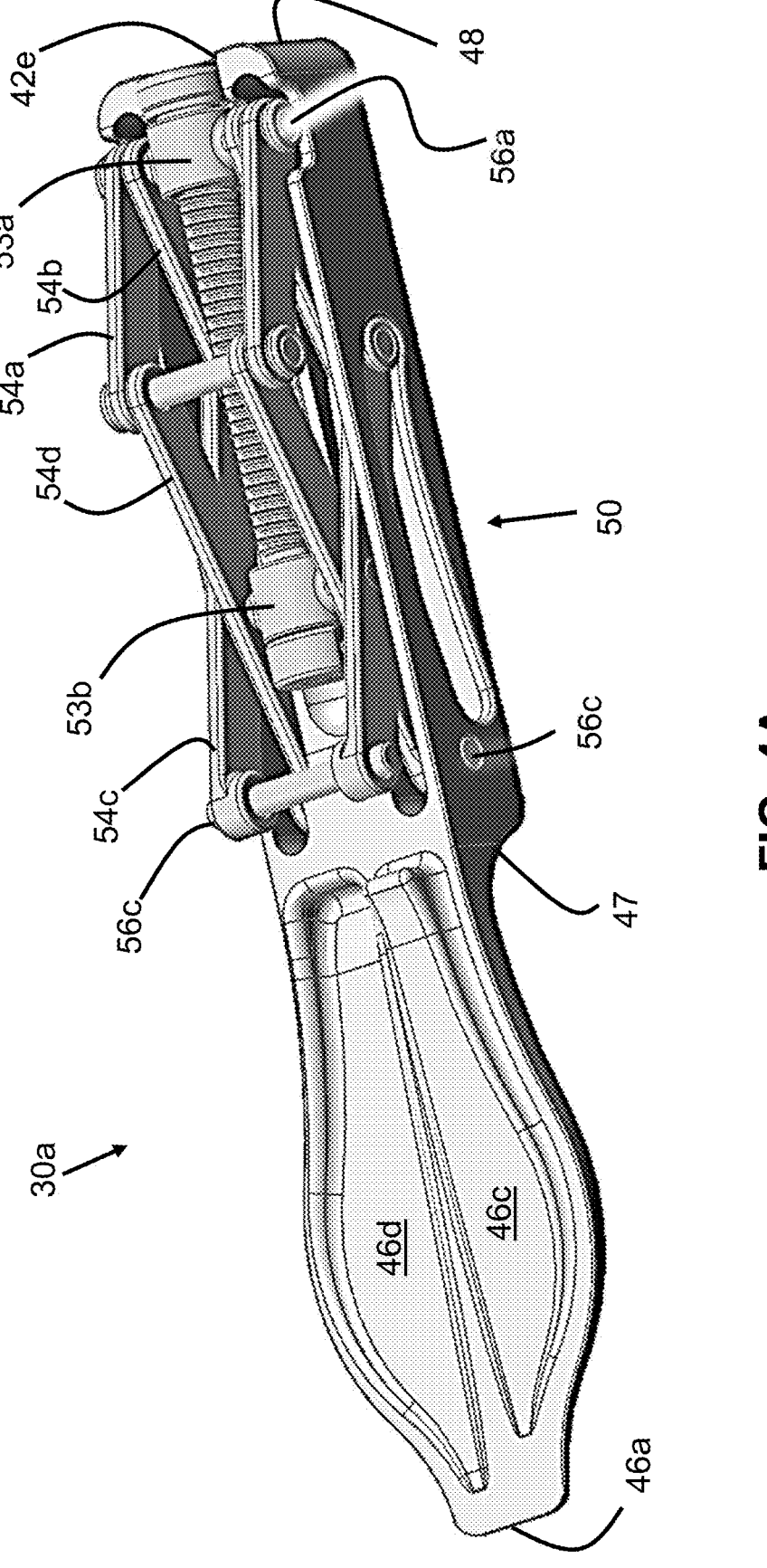
FIG. 4A is a left side, top elevational view looking downward at the apparatus of FIG. 3A with the top spreading member removed.

Referring FIGS. 4A and 5, it can also be seen that on the underside of each spreading member 40 are stiffening features 46c and 46d that extend on either lateral side along a longitudinal axis 31. As can be seen in FIG. 4, a stiffening rib 46c has a thickness that increases in the direction from distal tip 46 toward shoulder 47. In the region of shoulder 47, rib 46 has a thickness that increases the bending stiffness of the bone contact region 46. This rib 46 also preferably extends across the mating surfaces of the spreading member. The other side of the bone contact region 46 includes a receiving pocket 46d that has a gradually increasing depth.

As can be appreciated in viewing FIGS. 4A and 5, it can be seen that when two spreading members 40 are placed in the nested position, the stiffening rib 46c of the first member extends into a receiving pocket 46d of the second, opposite member. These stiffening features 46c and 46d provide a means to stiffen the bone contact region 46, while still maintaining a low overall thickness, as seen in the side view of FIG. 2. In that figure it can be seen that the top surfaces 40a in the bone contact region 46 present a wedge-shape. The inner contact or nesting surface 40b of each spreading member preferably extend in contact with one another around the entire periphery of the spreading member 40 (with the exceptions of cutouts 42d for the collar and pivot relief, and 42e for the driver access port).

Figure 3A:
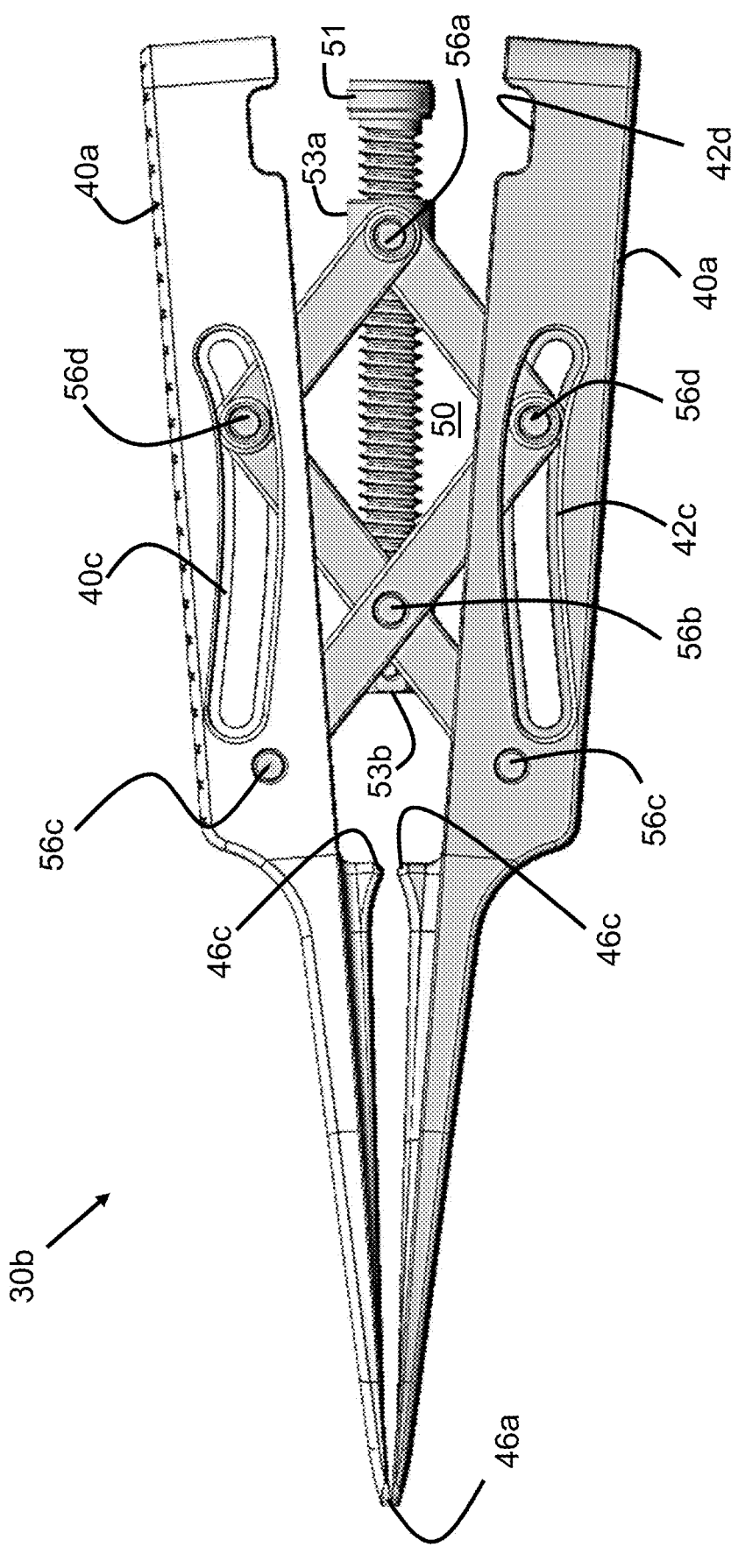
FIG. 3A is a left side elevational view of the apparatus of FIG. 2 shown in the partially opened or expanded position.

FIGS. 3A, 4, and 5 show the actuating device in the opened 30b position. It can be seen that device 30 includes means 50 for spreading apart the spreading members 40. In the embodiment shown, the means for actuation is a device 50 that includes a multi-link, multi-pivot scissors-type device. However, those of ordinary skill in the art will recognize that yet other means for actuation can be employed, including ratcheting-type mechanism, the use of a wedging device (either placed internally or inserted between inner surfaces of the spreading members 40), or others.

Referring to FIGS. 3, 4B, 4C and 4D, jacking device 30 includes an actuation device 50 that is located between the outer surfaces 40a of the spreading members 40. Likewise, this actuation device 50 can be seen in FIGS. 4A and 5 (fully nested) showing that the actuation device of a spreading device 30 according to various embodiments of the present invention preferably fit entirely between the top surfaces 40a and the lateral surfaces 40c. Those embodiments of the present invention that include a nestable actuation device permit the easy to grip outer envelope best seen in FIGS. 1 and 2.

Figures 3B, 3C:
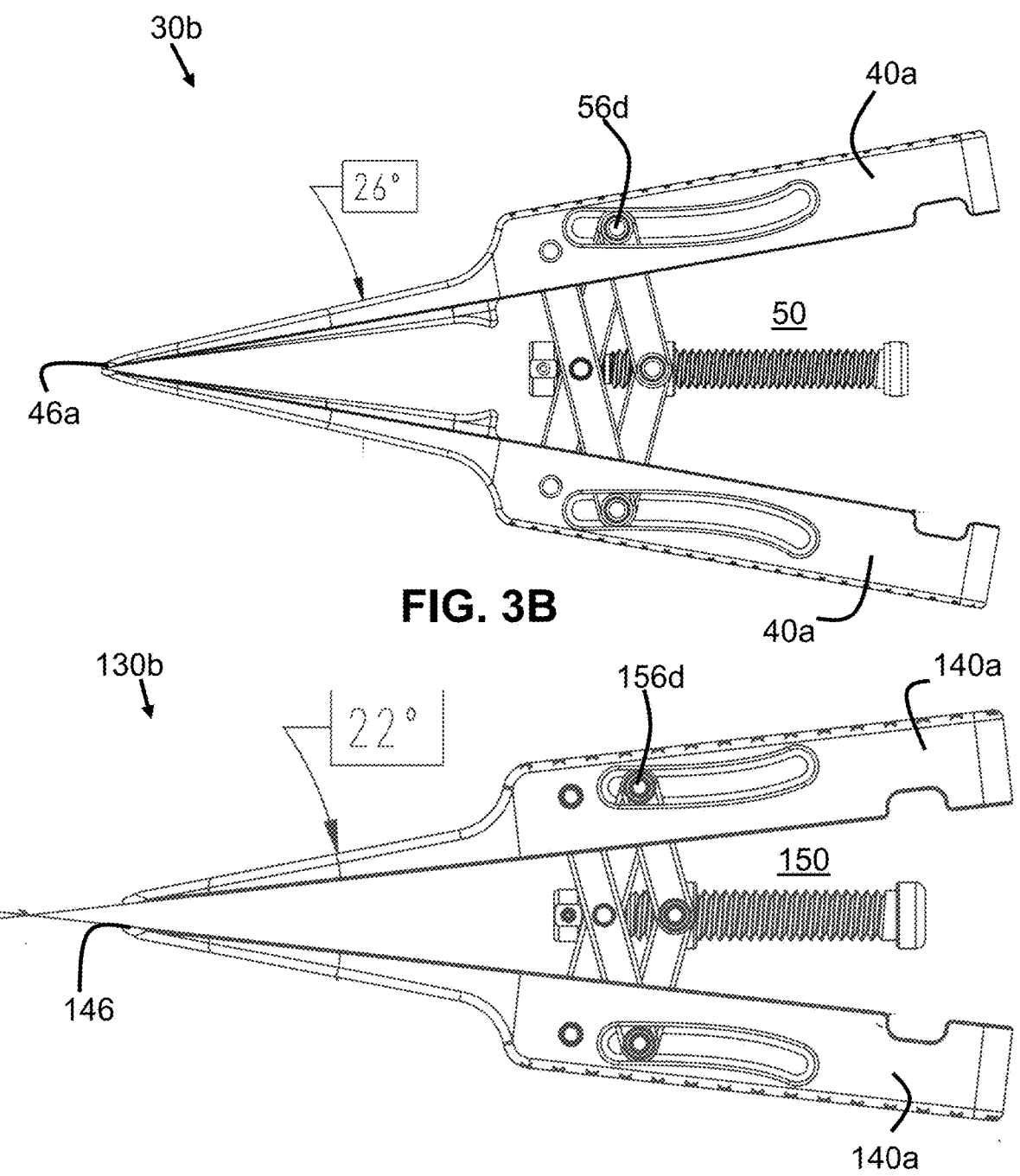
FIG. 3B is a side elevational view of the apparatus of FIG. 3A shown in a more open configuration.
FIG. 3C is a side elevational view of a spring device according to another embodiment of the present invention, and shown opened in a manner similar to that of FIG. 3B.

FIGS. 3A and 3B shows actuation device 50 in the partially opened position. Actuation device 50 is actuated to the open position by rotation of a central threaded actuator or driving member 51 in a first direction, with closing of the actuation device 50 being accomplished by rotation of that threaded actuator 51 in the opposite direction. Although what has been shown and described is a threaded actuator 51 that is arranged in a direction largely parallel to the longitudinal axis 31 of device 30, yet other embodiments contemplate rotary actuators (threaded and non-threaded) or linear actuators that have any orientation. It can be seen in FIGS. 3A and 4A that actuation device 51 is retained within an outermost or proximal most threaded collar 53 and an innermost or proximal most collar 53b. Each of these collars 53a and 53b are coupled by pivot joints 56a and 56b, respectively, to an arrangement of linkages 54.

Figures 4B, 4C, 4D:
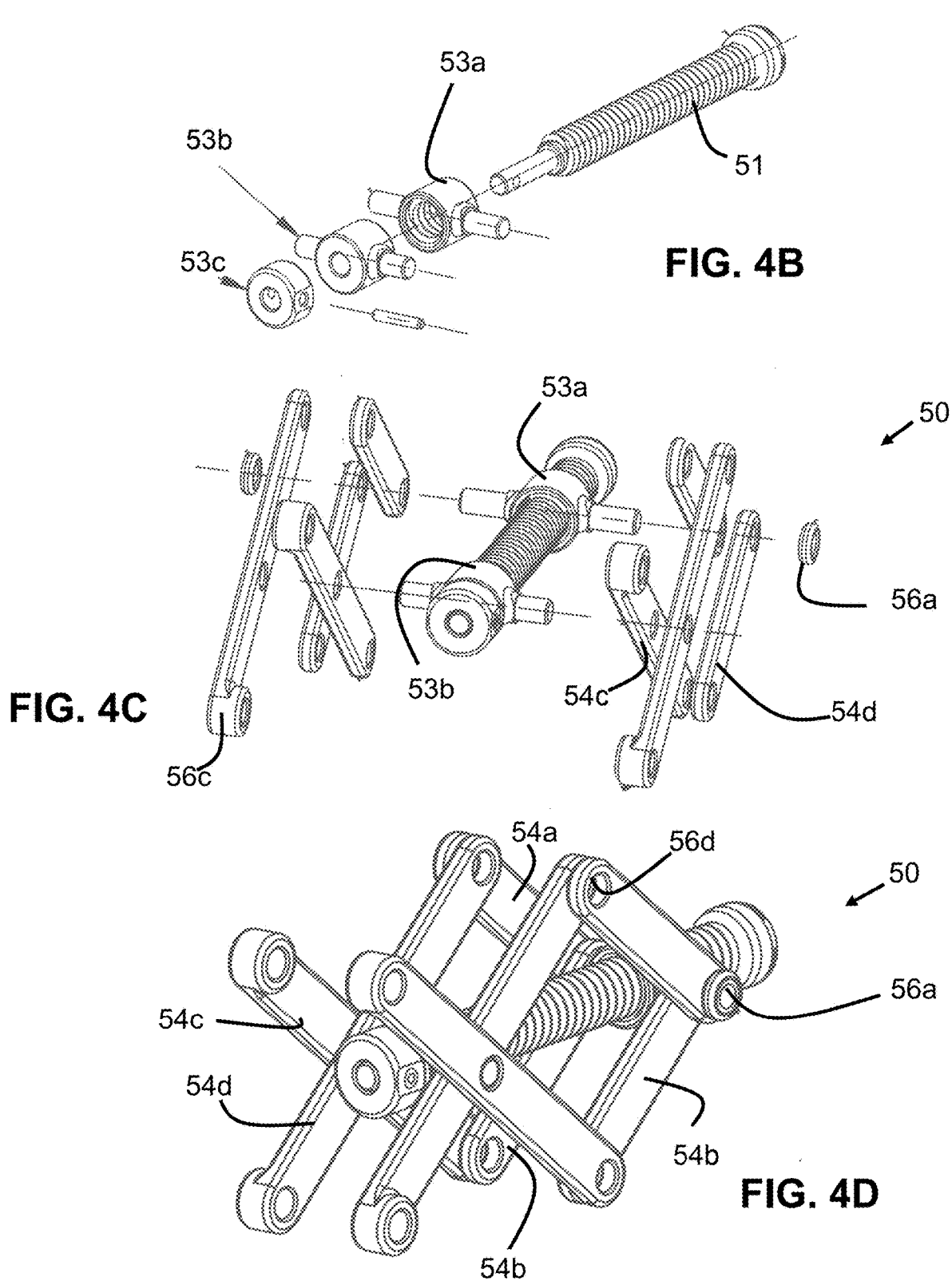
FIG. 4B is a perspective exploded representation of a portion of the actuation device of FIG. 4A.
FIG. 4C is a perspective exploded representation of a portion of the actuation device of FIG. 4A.
FIG. 4D is a view of the apparatus of FIG. 4C shown in a non-exploded view.

The linkage set 54 in one embodiment of the present invention includes, as best seen in FIGS. 4B, 4C, and 4D, a pair of outer and inner proximal linkages 54a and 54b, respectively, and a set of outer and inner distalmost linkages 54c and 54d, respectively. Referring to FIG. 5, it can be seen that the innermost linkage pairs b and d nest or collapse within the outermost linkage pairs a and c, respectively. Referring to FIGS. 4A and 5, it can be seen that in some embodiments of the present invention the set of links on one lateral side of the actuation device 50 are mirror images of a set of links on the other lateral side of the actuation device. However, various other embodiments of the present invention contemplate any arrangement of linkages that couple a threaded actuator to the spreading members 40.

As can be seen in FIGS. 4, the right and left lateral sides of the linkage sets are interconnected by pivots that extend laterally across the actuation device, as will now be described. Referring to FIGS. 3A and 4B, proximal links 54a and 54b are interconnected by a pivot axis 56a that links to collar 53a. The linkages 54a and 54d are interconnected by an axle to form a pivot joint 56d. Links 54d and 54c are interconnected by pivot joints 56b to the distalmost collar 53b. The links 54c and 54d are pivotally connected to the spreading members 40 by an axle that operates as pivot joints 56c. The movement of the links on one lateral side of device 30 are substantially the same as the movement of the links on the other lateral side.

Referring to FIG. 3A, it can be seen that rotation of driving member 51 changes the distance between collars 53b and 53a. Since the linkage set 54 is coupled to collar 53a, rotation of driving member 51 changes the angular relationship of the various links. The distalmost end of the linkage set is coupled to the side members by pivot axles 56c, therefore, rotation of driving member 51 changes the spacing between collar 53a relative to pivot axes 56c. As this distance changes, the spread of the links is governed by the movement of pivoting cam followers 56d within the cam profile 42c of the spreading members.

The cam profile 42c is adapted and configured such that as the actuation device opens the proximal most end of device 30, the distalmost tips 46a of the spreading members remain in close contact, such that the outer surfaces of the bone contact region form a V-shape. Therefore, when spreading device 30 is placed in an incision in a bone, actuation of the device to an opened position will result in a wedge-shaped separation of the cut bone surfaces.

In some embodiments, the cam and cam profile are adapted and configured to provide a pivoting apart of the spreading members with a single degree of freedom, such as rotation of one member relative to the other member, with the rotational axis being located at a distal most end. Referring to FIG. 3C, it can be seen that a spring device 150 according to another embodiment of the present invention permits the distalmost ends to spread apart as the proximal most, hammering end spreads apart. This versatility in the manner of spreading is permitted by modeling the spreading members X40 spaced apart in the desired relationship, and then predicting the required location to achieve that spreading member position with a particular actuation device X50. By repeating this process for a variety of relative positions of one spreading member X40 relative to the other spreading member X40, a range of cam follower pivotal points X50d are predicted. This range of cam follower points can then be spline-fit together, to form the required cam groove.

Still further, some embodiments contemplate a hinge interconnecting the two distalmost tips of the spreading member. Still further embodiments contemplate a spreading geometry in which the spreading members pivot or angularly rotate relative to one another as the actuation mechanism is actuated, and further that the spreading members simultaneously spread apart by a predetermined displacement.

Figure 6:
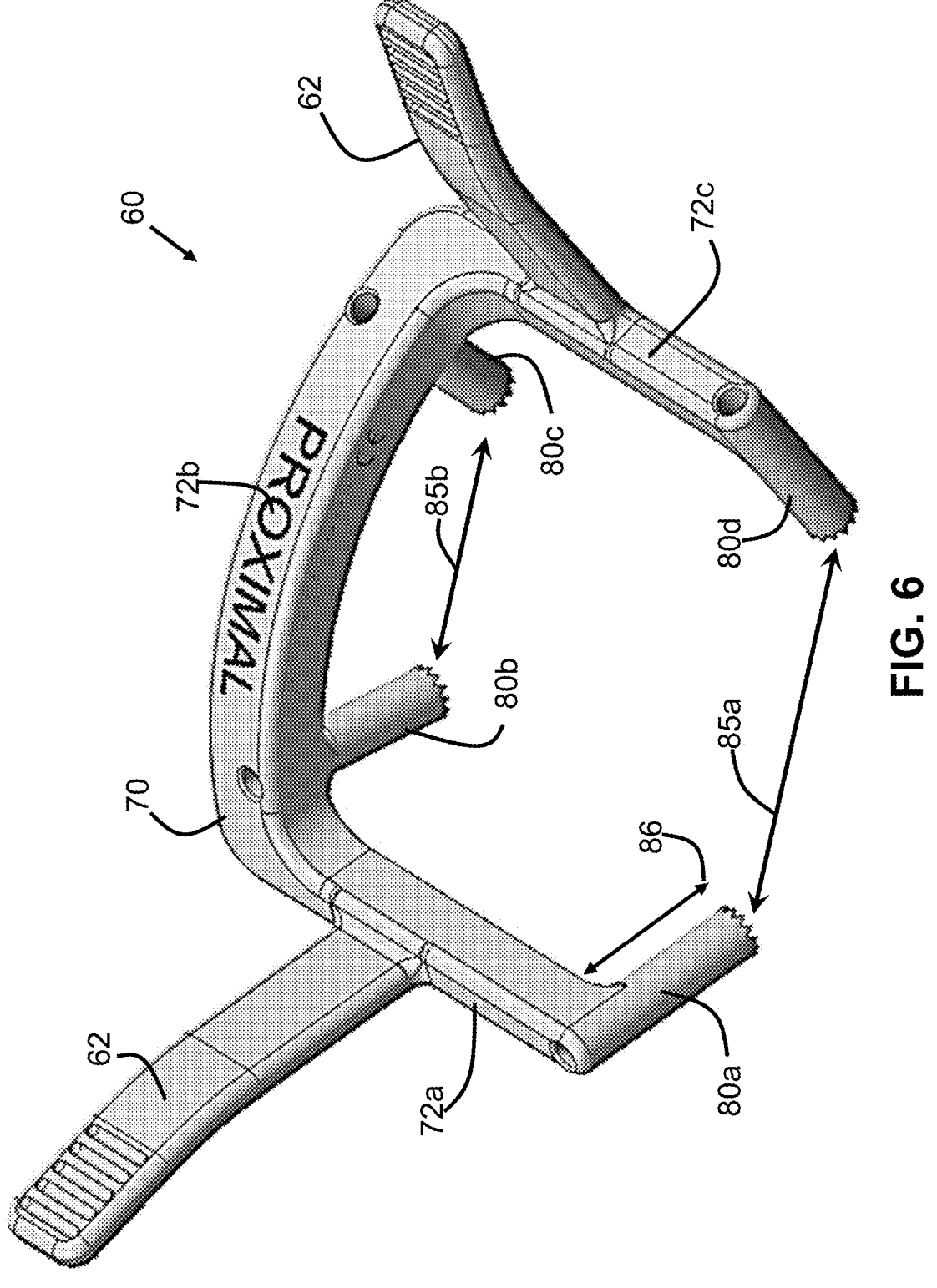
FIG. 6 is a top, right side perspective scaled CAD representation of a bridging device or guiding device according to another embodiment of the present invention.

FIGS. 6-8 show various views of a bridging devices 60 and 160, according to various embodiments of the present invention. Those of ordinary skill in the art will recognize that many of the comments made to describe bridging device 60 apply either specifically or generally to bridging device 160, as will be discussed. Device 60 is preferably but not necessarily a one-piece structure that includes a peripheral, interconnecting wall 70 that interconnects a plurality of standoff posts 80. In one embodiment, the interconnecting peripheral wall 70 wraps around a largely open central aperture 78 that is adapted and configured to temporarily assist in an osteotomy, as will be shown and described later. Wall 70 preferably includes an opening 76 through which the opened interior 78 can be accessed. Preferably, the width of the opening 76 is about the same as the width 78a of the aperture 78, such that a device that can fit through opening 76 can also be accommodated within aperture 78. Aperture 78 has a depth 78b that is sufficiently large to maintain within it a jacking device such as device 30 in an opened position.

Figure 7A:
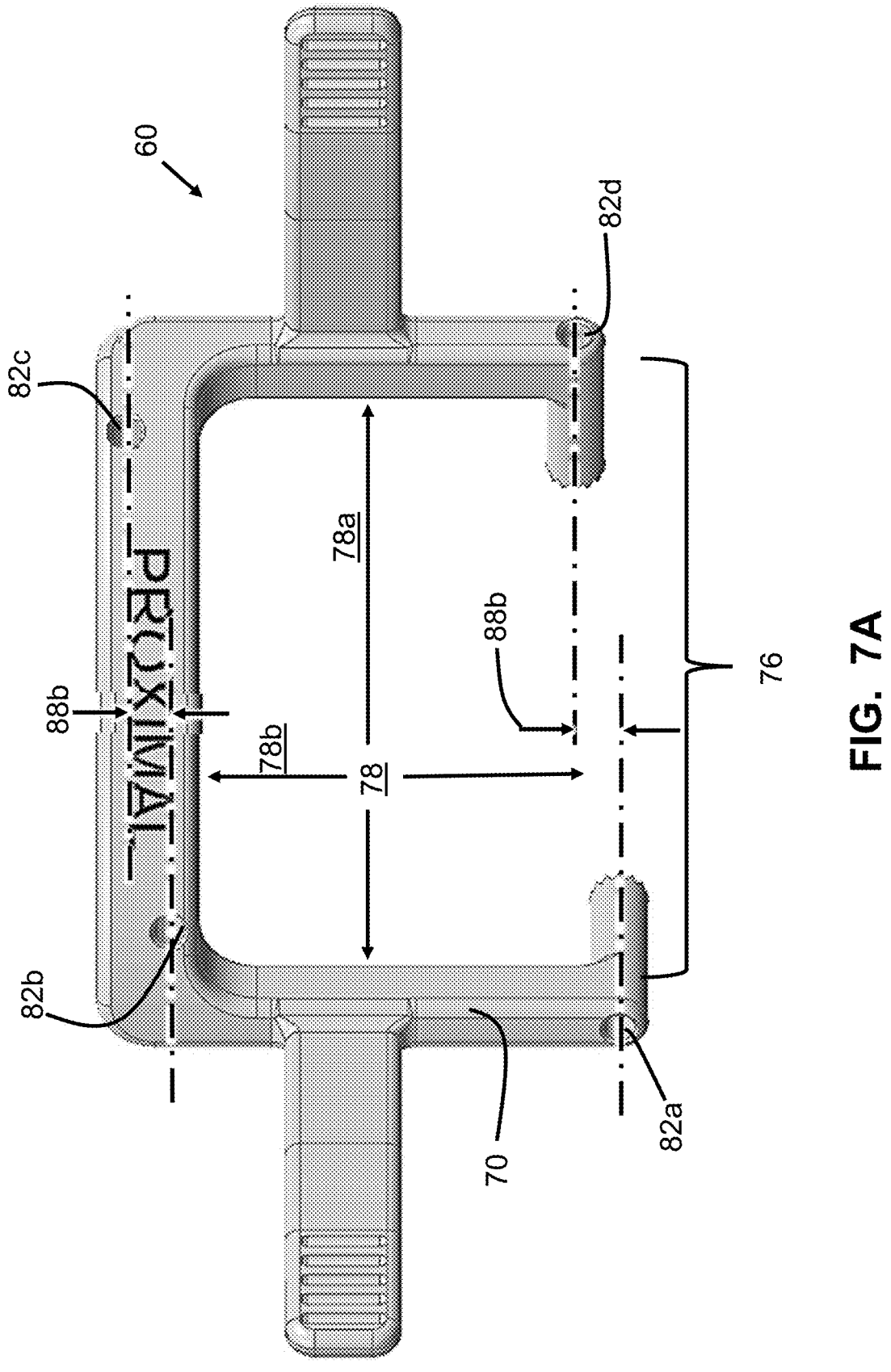
FIG. 7A is a top elevational view looking downward at the apparatus of FIG. 6.
Figure 7B:
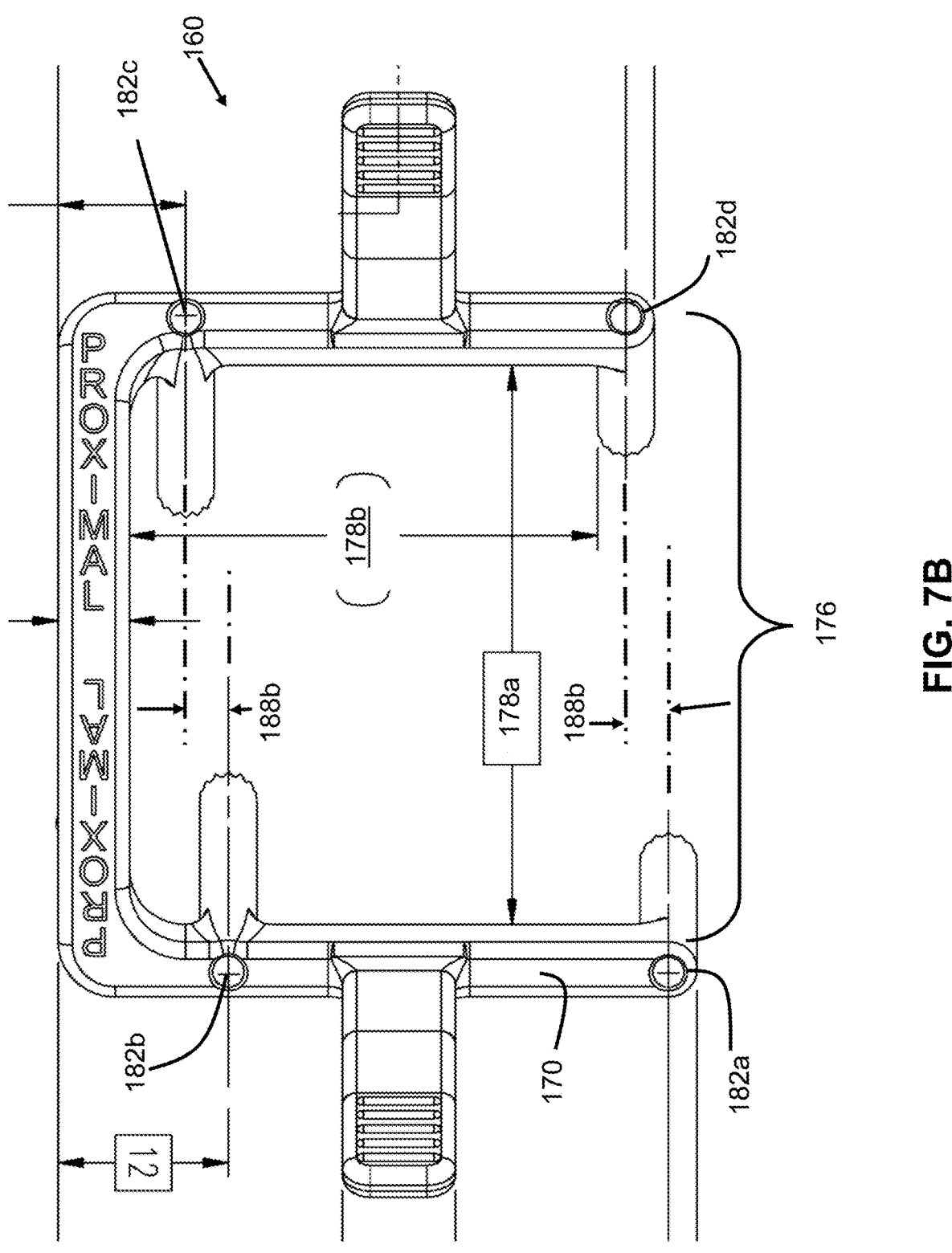
FIG. 7B is a top elevational view looking downward of a bridging device according to another embodiment of the present invention.
Figure 8A:
FIG. 8A is a frontal plan view of the apparatus of FIG. 6.
Figure 8B:
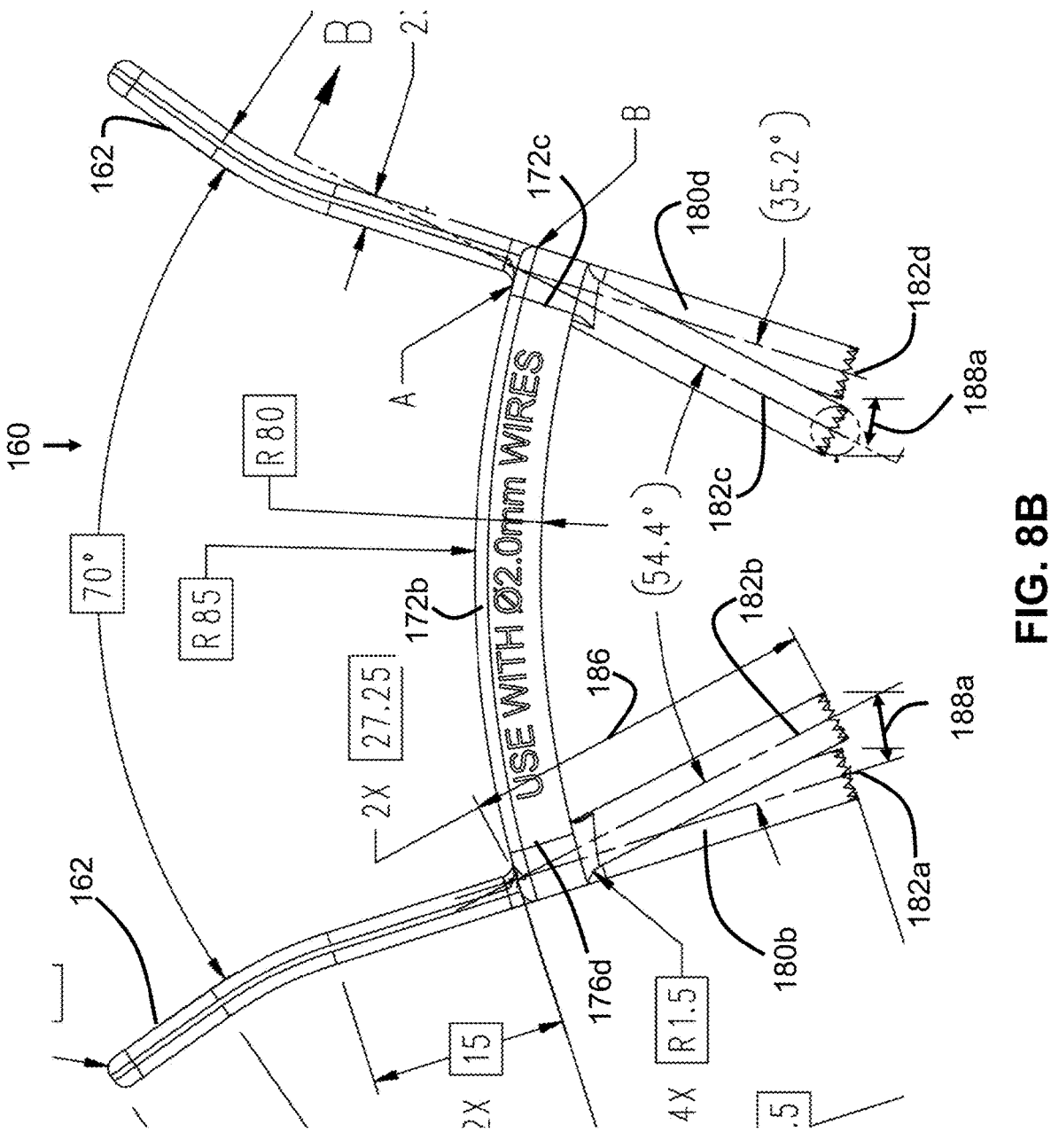
FIG. 8B is a frontal plan view of the apparatus of FIG. 7B.

FIGS. 7A and 8A show top and side views, respectively, of bridging device 60. FIGS. 7B and 8B show the same views of a bridging device 160 according to another embodiment of the present invention. Comparing FIGS. 7A and 7B, it can be seen that the bores 82 and 182 useful for attaching the bridging devices to the incised bone, have different relative spacings, and also different spacings relative to their respective interconnecting walls 70 and 170, respectively. In comparing FIGS. 8A and 8B, it can further be seen that the standoff posts 80 and 180 likewise show different interrelationships of one post relative to another, and further of the posts relative to the interconnecting wall.

In one embodiment, wall 70 is supported by a plurality of standoff posts 80 that support wall 70 above the surface of a bone. In one embodiment, wall 70 includes a pair of left-side posts 80a and 80b interconnected by a first wall segment 72a, a laterally spaced apart pair of posts 80b and 80c interconnected by a second wall segment 72b, and an axially separated pair of posts 80c and 80d interconnected by a third wall segment 72c. As shown in FIGS. 6 and 7, in one embodiment the wall 70 is in an approximate rectangular shape, and includes a post at each "corner" of the wall. However, in other embodiments, wall 72 can have a curved, circular, or triangular plan shape, as examples. In a curved or circular plan shape a sector of the curved or circular plan form is removed to allow access to a curved or circular interior aperture. With a triangular plan form, a segment of the triangular shape is not present, thus providing an opening through which a central aperture can be accessed. It is also understood that these embodiments can be combined in a plurality of ways, such that a triangular arrangement of posts can support a rectangular or curved wall. Preferably, a bridging device includes at least two standoff posts, such that these posts are arranged on opposite sides of an incision in a bone, as will be shown later.

Referring to FIG. 8A, it can be seen that the standoff posts 80 have one end 84 adapted and configured for contact with the bone surface, and the other end of the post supporting the wall 70, the separation of the ends of the posts being greater than the width of a bone plate that will be connected across the incision (and as will be described later). The bone contact surface 84 can be of any configuration, although in the embodiment shown in FIG. 8A the contact surface 84 is a roughened surface, such as a surface including a plurality of circumferential teeth. The roughened nature of contact surface 84 is adapted and configured to resist slippage on the surface of a bone. Still further embodiments of the present invention include a peripheral wall that is spaced at any position along the length of the supporting posts. As one example, the peripheral wall could be located closer to the bone surface (closer than as shown in FIG. 8), and could still further include a section of posts extending still further above the top of the wall.

FIG. 8A also shows that the posts 80 support the underside of the wall 70 by a clearance height 86. The height of these posts are adapted and configured to establish this clearance height 86 such that a bone plate in contact with the surface of the incised bone can slide underneath the bottom of wall 70. Still further, the standoff posts 82b and 82c are separated apart by a lateral distance such that a bone plate can be received between these standoff posts. Referring to FIG. 7A, it can be seen that the lateral distance between posts 82b and 82c can be less than the distance between posts 82a and 82d, in consideration of the accommodation of bone plates having varying widths.

Referring to FIGS. 7A and 8A, it can be seen that in one embodiment the standoff posts 80 each define an interior bore 82 that is a through bore that extends completely through the post. These bores 82 are adapted and configured to receive therein a locating guide wire or a threaded guidewire to assist in the placement of the bridge 60 on the incised bone, preferably spanning both sides of the incision. Preferably, bores 82c and 82d are on opposite sides of the incision, as are bores 82a and 82d. Although the use of a guidewire has been shown and described, yet other embodiments utilize fastening devices such as long screws, nails, or any kind of fixation device. Still further, the posts themselves could have a sharpened end that comes into contact with the bone, and still further could be hammered into the bone.

FIGS. 7A and 8A show that these bores 82 are arranged to have an angular or lateral spacing apart 88a, as best seen on FIG. 8A. Further, pairs of the standoffs and bores are arranged to be axially spaced apart by a distance 88b, as best seen in FIG. 7A. Comparing FIGS. 8A and 8B, it can be seen that whereas the bores 82 are spaced apart by an angular width that decreases in a direction toward the bone, bridging device 160 instead has an angular width 188a between attachment posts that diverges in a direction toward the interior of the bone. It can also be seen that the centerlines 182 in one embodiment intersect along lines that are generally parallel (as best seen from above in FIG. 7B). It is understood that the spacing apart in either the lateral (angular) or axial distances can be different between different pairs of bores, and not necessarily the same spacings as indicated in FIGS. 7A and 8A. Further, FIG. 8A shows that the bores 82 are generally aligned to roughly intersect the center of the bone. Commensurately, the shape of the interconnecting wall segment 72b is preferably curved so as to roughly parallel the surface of the bone.

Referring to FIG. 7A, it can be seen that the bores 82a and 82d are spaced apart by a distance 88b, and are preferably not coplanar. In some embodiments, distance 88b helps insure that the guide pins inserted through their bores and into the bone do not intersect directly with each other inside the bone. In some embodiments, the positioning of the attachment posts are adapted and configured such that the bore centerlines do not intersect with other bore centerlines inside the bone. Further, in this manner, the stress fields in the bone created by the temporary attachment with threaded guide wires are spread apart, with a lower maximum stress in the bone cortex near the center. Bores 82b and 82c are spaced apart by a distance 88b (which can be different than the spacing of 82a relative to 82d) that likewise reduces the stress field in the bone proximate to the area of the bone in the middle of the incision. Viewing both FIGS. 7A and 8A, it can be seen that a polygon connecting the periphery of the bores 82a, 82b, 82c, and 82d does not include any right angles. However, comparing FIGS. 7A and 7B, it can be seen that the bores 182a, 182b, 182c, and 182d in some embodiments are arranged as a parallelogram, with the opposite sides of the wall being generally parallel.

A pair of handles 62 extend upwardly and outwardly from wall 70. These handles are preferably spaced apart and angularly outward such that they permit ease of handling when guide wires are extending out of the bores 82.

One method of performing an osteotomy with devices according to one embodiment of the present invention will now be described. It is understood that the devices described herein have usefulness independent of the following surgical procedure, or any surgical procedure. Place the desired plate 24 on the lateral aspect of the distal femur 10 to locate the start point of the osteotomy. The start point of the osteotomy should be located near the distal end of the solid portion of the plate 24. Consideration should be taken to ensure enough real-estate in the distal fragment for the three-hole cluster of screws.

Figures 9, 10:
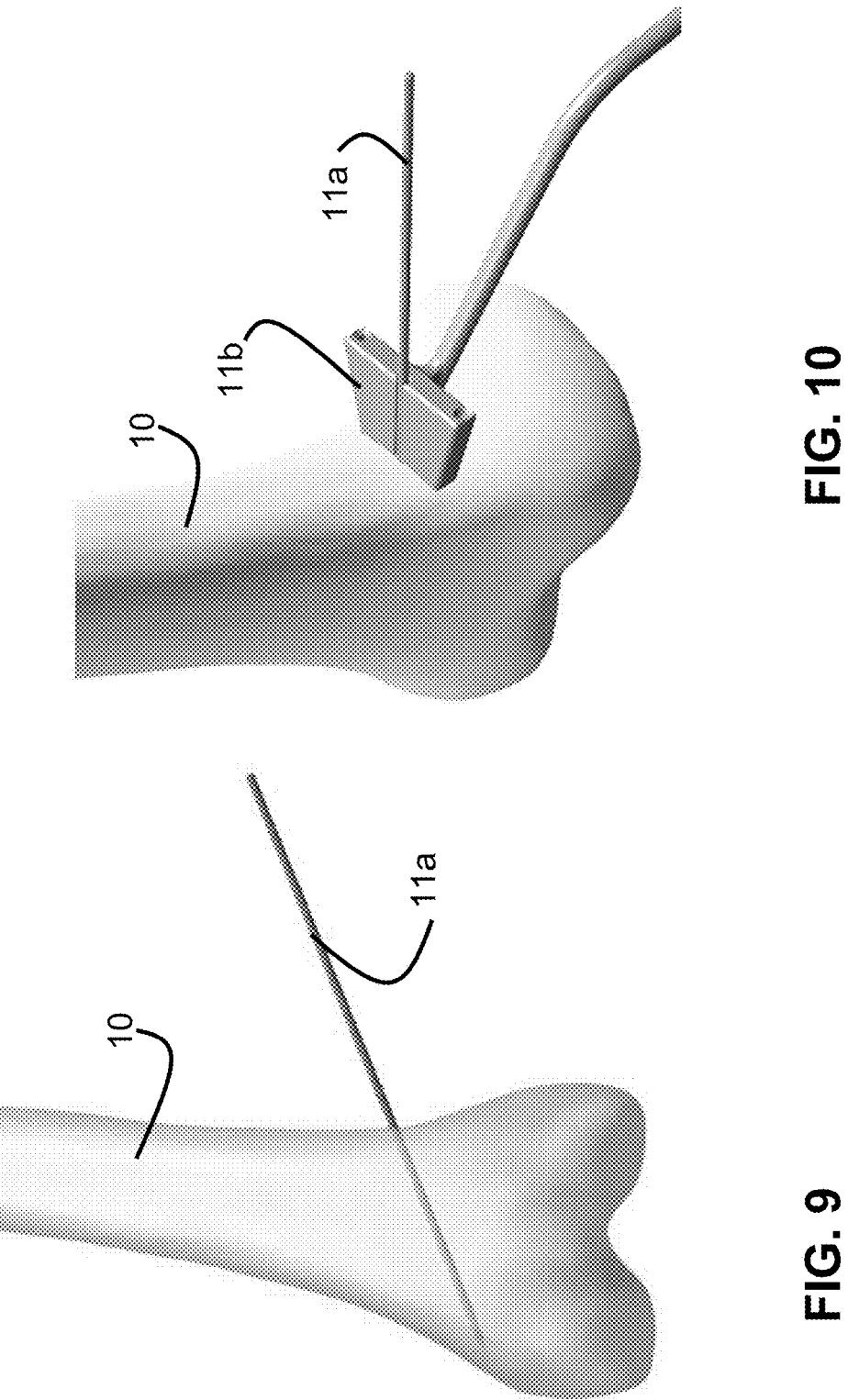
FIG. 9 shows a long bone 10 needing an angular correction.
FIG. 10 is a view of the bone of FIG. 9 showing a wire guide and a cutting guide on the long bone.

Insert an initial 2.0 mm guide wire 11a at the start point of the osteotomy, located centrally about the metaphysis/diaphysis on the lateral femur. Using fluoroscopy, advance the guide wire towards the medial epicondyle, keeping the tip of the guide wire at least 1 cm away from the medial cortex (see FIG. 9).

Place the cut guide 11b over the 2.0 mm guide wire 11a, through the central 'in-line' cannulation. Ensure the handle of the cut guide is parallel with the diaphysis of the femur to prevent unwanted flexion or extension in the osteotomy. Insert two 2.0 mm guide wires 11a in the peripheral holes of the cut guide, and remove the initial central guide wire 11b (see FIG. 10).

Utilizing a sagittal saw (not shown), start the osteotomy 12 through the lateral cortex. Osteotomes can be used to complete the osteotomy to the appropriate depth. To minimize the risk of fracturing the hinge, approximately 1 cm of medial bone should be preserved.

Figures 11A, 11B:
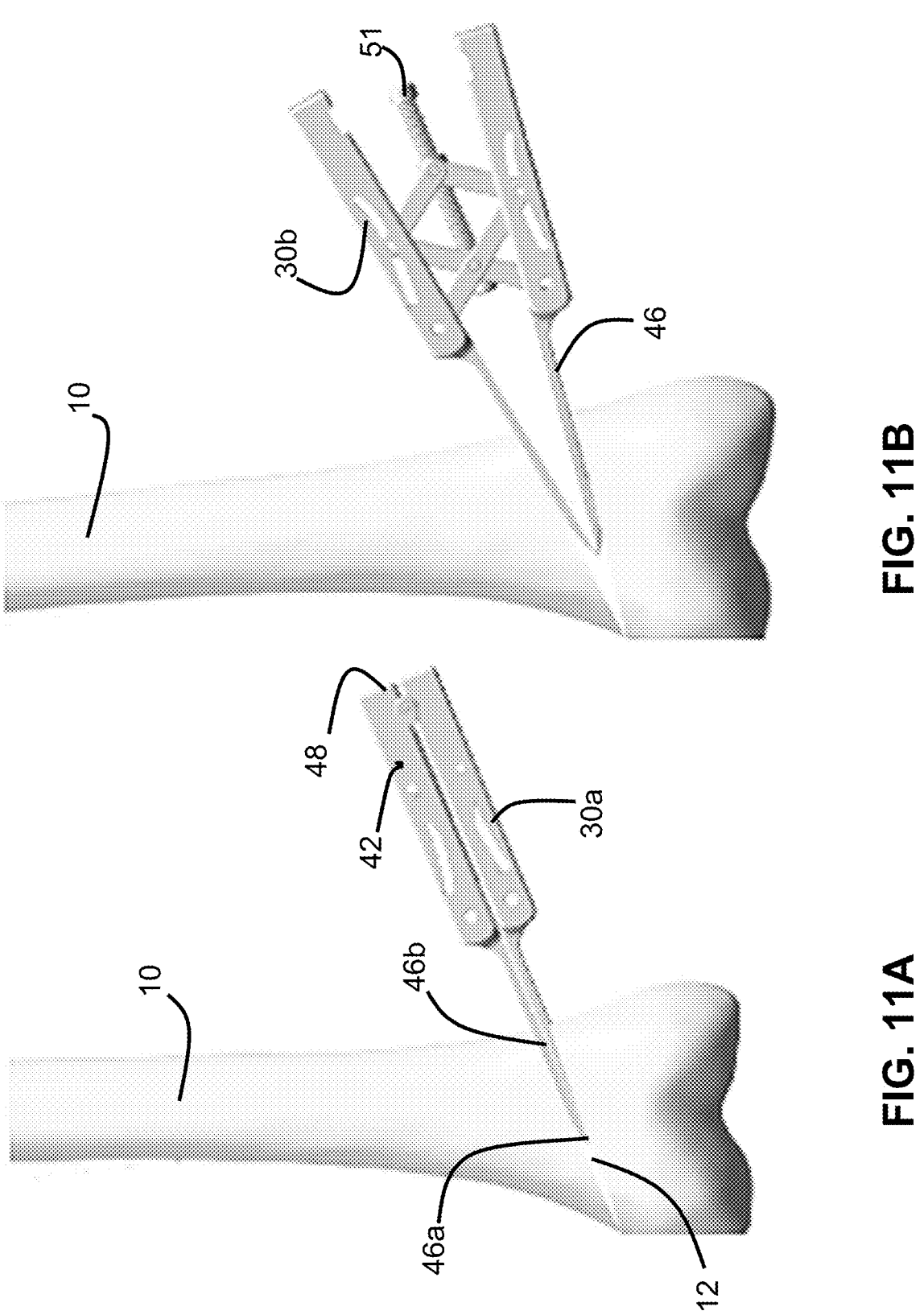
FIG. 11A is a view of the bone after an incision has been made, and prior to spreading apart the bone surfaces.
FIG. 11B is a view of the bone of FIG. 11A after the wedge opening has been made.

Referring to FIGS. 11A and 11B, insert the jacking device 30 into the osteotomy 12, and use a driver to open the jack 30 to the targeted correction angle. This step should be performed slowly to reduce the risk of medial cortex fracture. Fluoroscopy should be used to check limb alignment and ensure that the desired correction angle has been achieved.

Referring to FIG. 11A, it can be seen that in the fully nested position 30a the jacking device 30 provides a convenient chiseling shape to facilitate the opening of the osteotomy. The closed shape 30a can be inserted with the distalmost tip 46a being presented to the incision 12. The gripping regions 42 provide a convenient hand hold for the surgeon to push the nested spreading members 40 past the bone cortex and into the cancellous region of the bone. If necessary, the spreading device 30 includes a hammering end 48 that is adapted and configured to receive impacts from a hammer. Because of the ability of the two halves of the jack to nest tightly against one another, with the actuation device contained therein, a jacking device 30 according to some embodiments of the present invention require less volume around the patient, thus facilitating movement of the physician and other medical professionals, as well as various instruments.

Referring to FIGS. 12A, 12B, 12C, and 12D, place the Bridge 60 over the jack 30a, with the bottom of the device 60 oriented over the distal femur. Insert four 2.0 mm guide wires 83 into the cannulations 82 of the Bridge. After confirming desired correction angle, collapse the jack 30b using a suitable driver and remove.

Comparing FIGS. 12A and 12B, it can be seen that the opening 76 in the peripheral wall is adapted and configured to permit easy movement of the bridge 60 over the inserted jacking device 30b. It can been seen that the various standoff posts 80 are separated a sufficient distance so as to not interfere with the lateral surfaces 40c of the spreading members 40. In addition, there is sufficient axial depth 78b of the central aperture 78 to receive therein some or all of the protruding jacking device 30b, and further sufficient lateral width 78a to accommodate the width of the gripping end 42.

Further, comparing FIG. 12C with FIG. 6, it can be seen that standoff posts 80a and 80d are located on the same side of the incision 12, but on opposite sides of the protruding jack 30b. Standoff posts 80b and 80c are located on the same, opposite side of incision 12, and are located on either side of jacking device 30b. The corresponding bores 82 of the standoff posts 80 support the guide wires 83 in the angular representations seen in FIG. 8. FIG. 12C shows that bridging device 60 provides a temporary securement of the opened incision 12, but further that the guide wires 83 and the handles 62 are located out and away from the jacking device 30b.

Figure 12D:
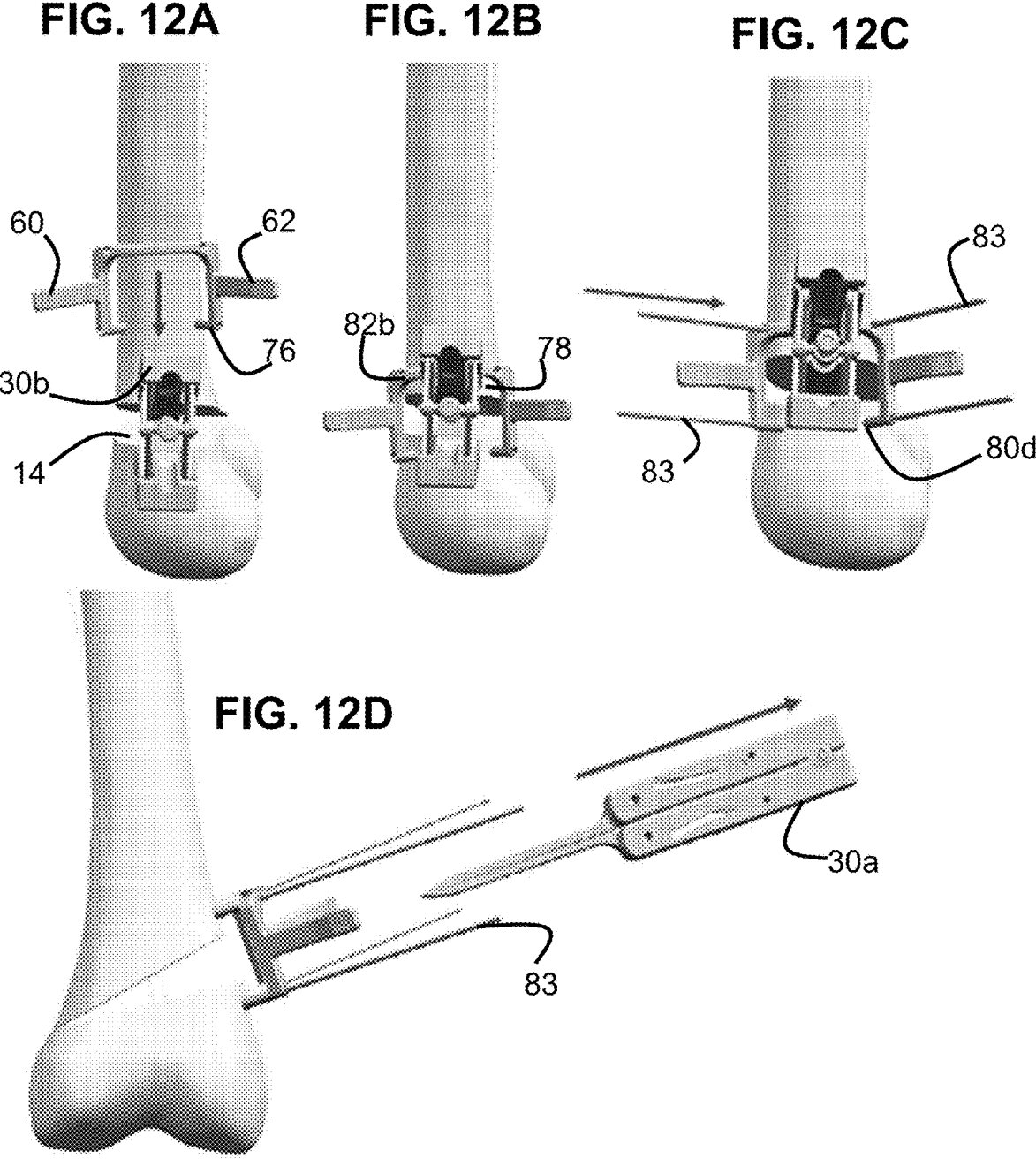
FIG. 12D shows the spreading device in the closed position being removed from the wedge.

Referring to FIGS. 12C and 12D, it can be seen that this placement of the standoff posts, bores, guide wires, and make for easy nesting and collapsing of the device 30a as well as its subsequent removal from the incision 12. With the spreading device 30 removed, the central aperture 78 presents to the surgeon a relatively large, clear area through which there is access to the osteotomy 12.

Referring to FIGS. 13A, 13B and 13C, insert the Graft Measurement Handle 16 into the osteotomy 12 and read the amount of opening in millimeters at the lateral cortex. Prepare the graft 18 and insert it into the osteotomy 12. Referring to FIG. 13B, it can be seen that bridging device 60 permits significant, unimpeded access through aperture 78 for measurement of the wedge opening, as well as for subsequent placement of the graft material 18.

Figures 14A, 14B:
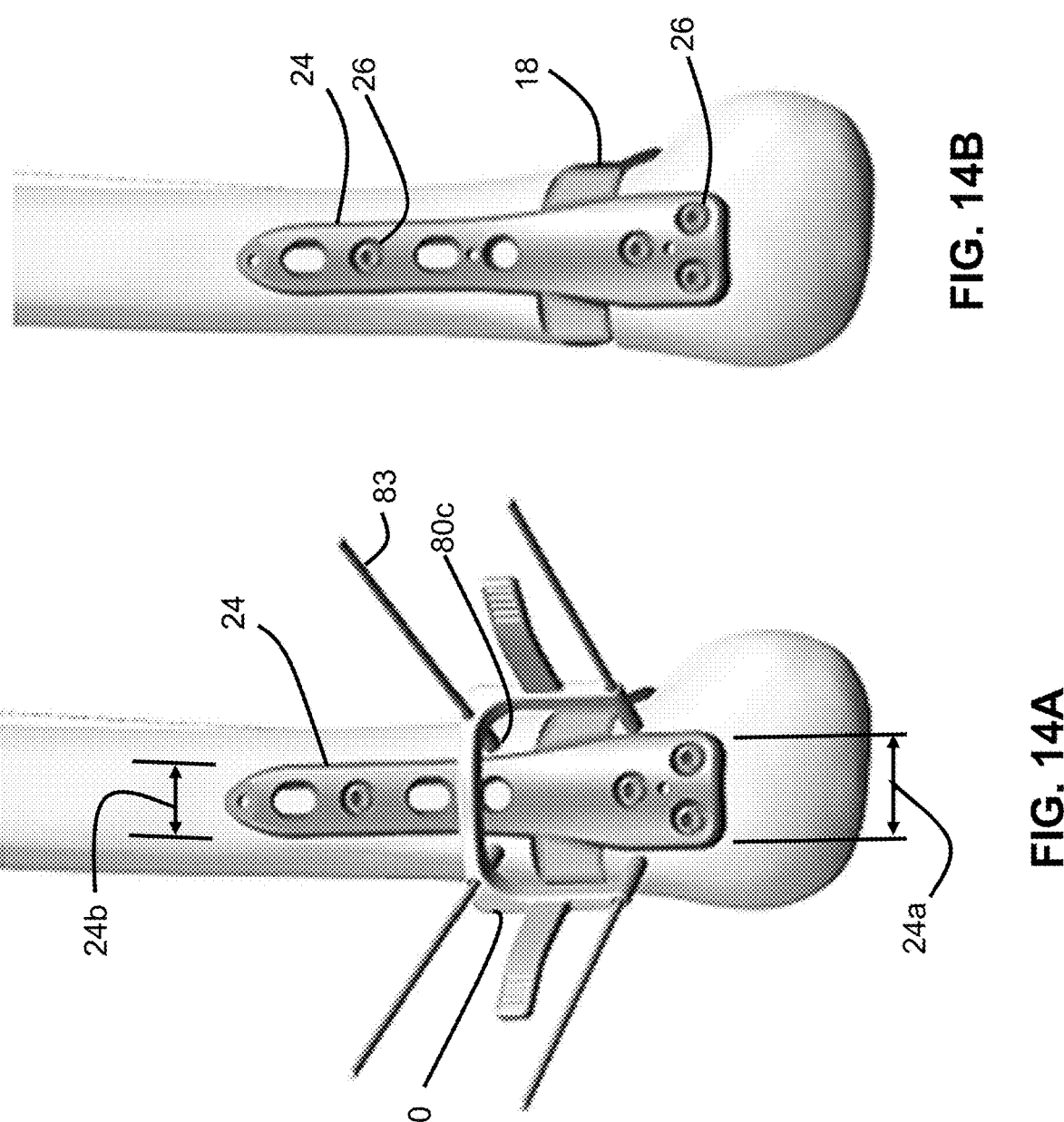
FIG. 14A shows the bone of FIG. 13B with a bone plate installed.
FIG. 14B shows the bone of FIG. 14A with the bridging device removed.

As best seen in FIGS. 14A and 14B, place the desired implant under the bridge 60, starting distally to proximally. Insert the implant screws 26.

Referring to FIGS. 14A and 6, it can be seen that the bridging device 60 is adapted and configured to permit clearance between the underside of the wall and the top surface of the bone plate 24. Therefore, the plate can be inserted easily over the incision 12 while the bridging device 60 is in place and in contact with the bone surface. It is to be understood that the clearance 86 seen in FIG. 8A can be of any dimension that permits the receiving of the bone plate between the underside of the interconnecting wall 72b and the top surface of the bone. Further, it is understood that wall 70 need not be at the same elevation above the bone surface. Yet other embodiments include a bone plate 60 that has lateral sides 72a and 72c that are closer fitting to the bone surface than the interconnecting segment 72b.

FIGS. 14A and 6 also show that the head width 24a of the bone plate is less than the head width allowance 85a between posts 80a and 80d. Likewise, the width of the portion of the bone plate heel 24b that is inserted between posts 80b and 80c is less than the heel allowance width 85b. Therefore, bone plate 24 fits easily within an under bridging device 60, ad further permits sufficient access for insertion of the fasteners 26 to attach the bone plate 24 to the bone 10.

Figures 15, 16:
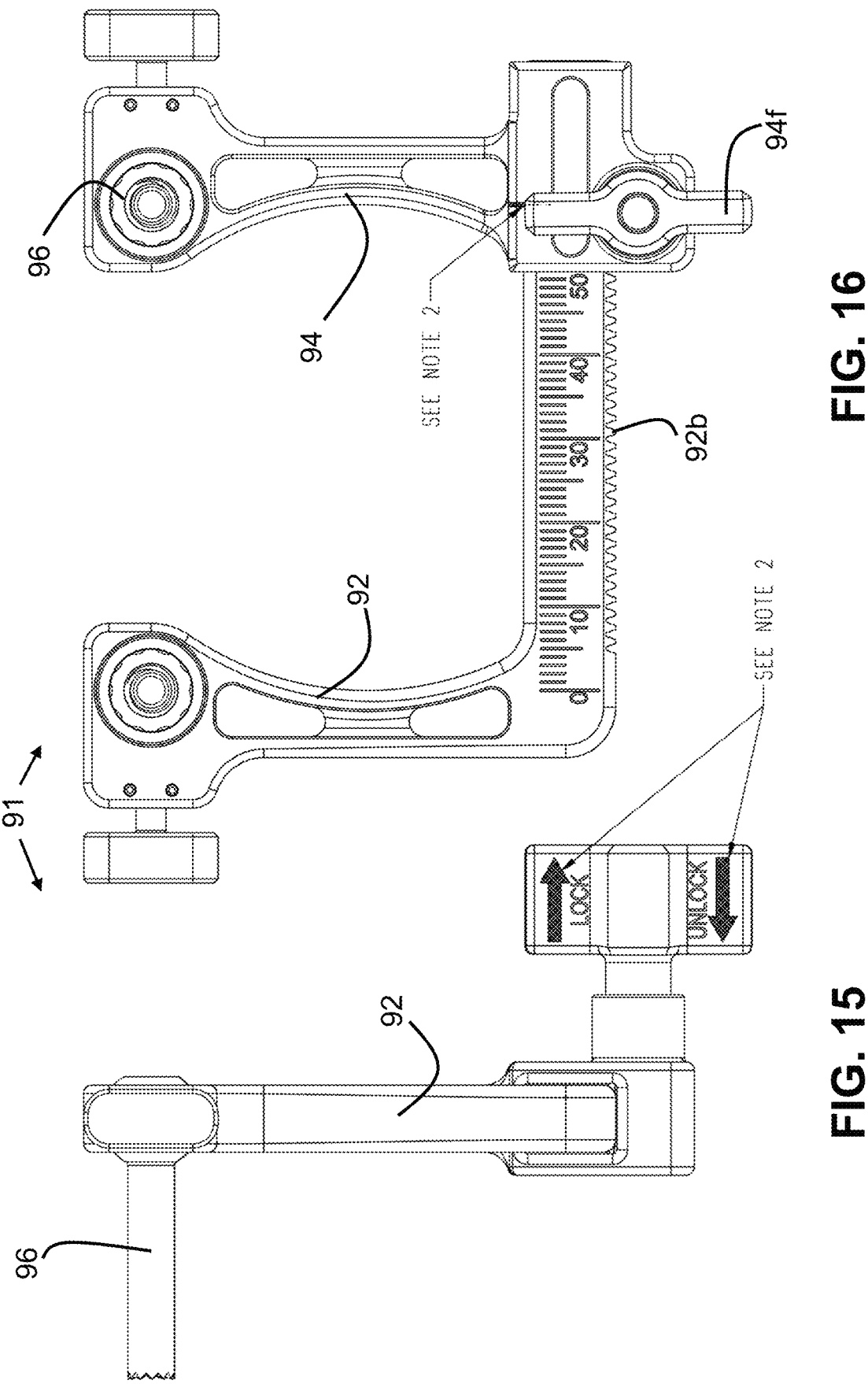
FIG. 15 is a CAD line drawing of a side elevational view of a portion of an adjustable bridging and distraction device according to another embodiment of the present invention.
FIG. 16 is a CAD line drawing of a front elevational view of the apparatus of FIG. 15.
Figure 17:
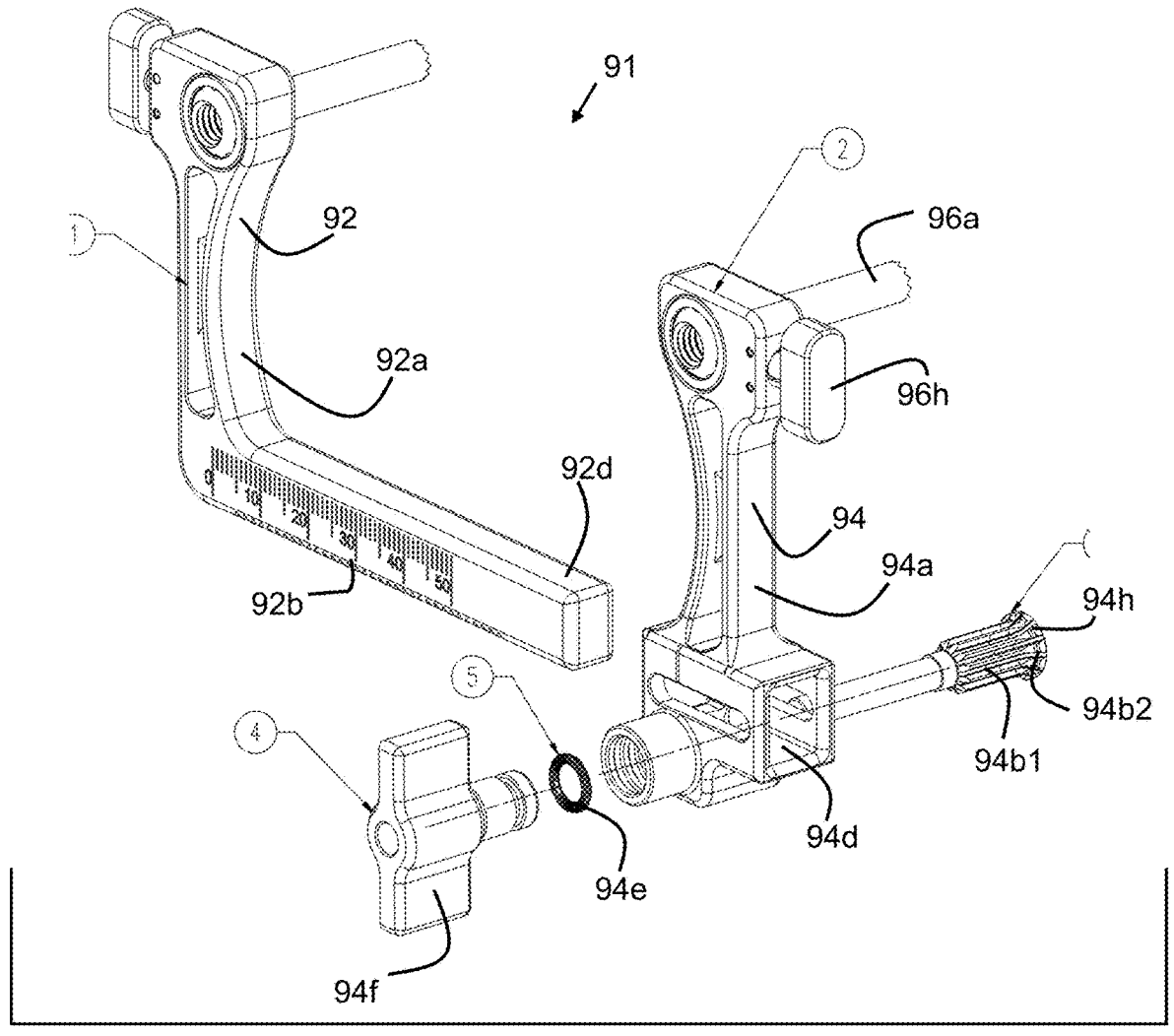
FIG. 17 is a CAD line drawing of a front and side perspective exploded representation of the apparatus of FIG. 15.
Figures 26, 27:
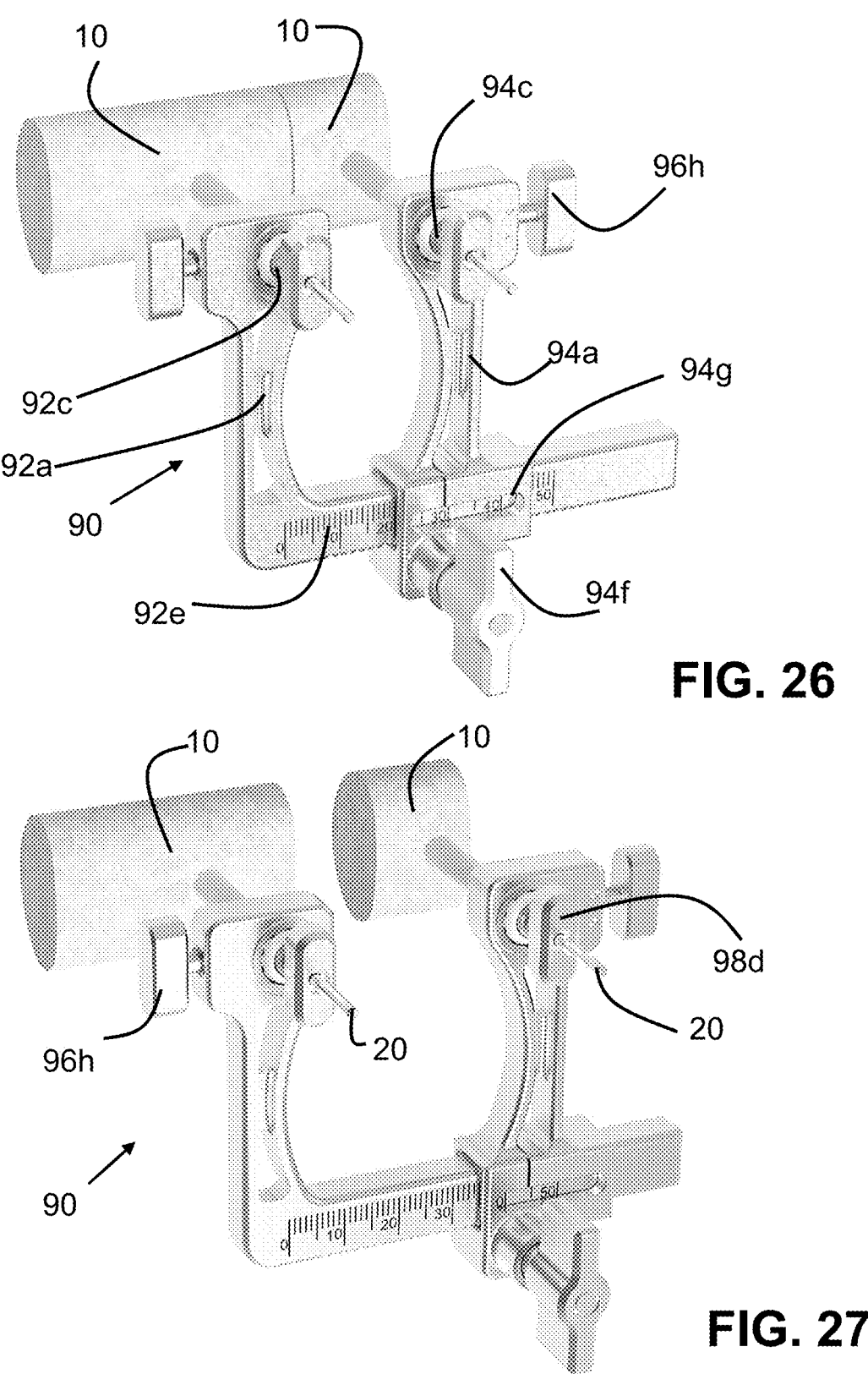
FIG. 26 is a CAD perspective representation of a bridging and distraction apparatus 90 shown attached to bone segments.
FIG. 27 shows the apparatus of FIG. 26, with the two bone segments being separated.
Figure 28:
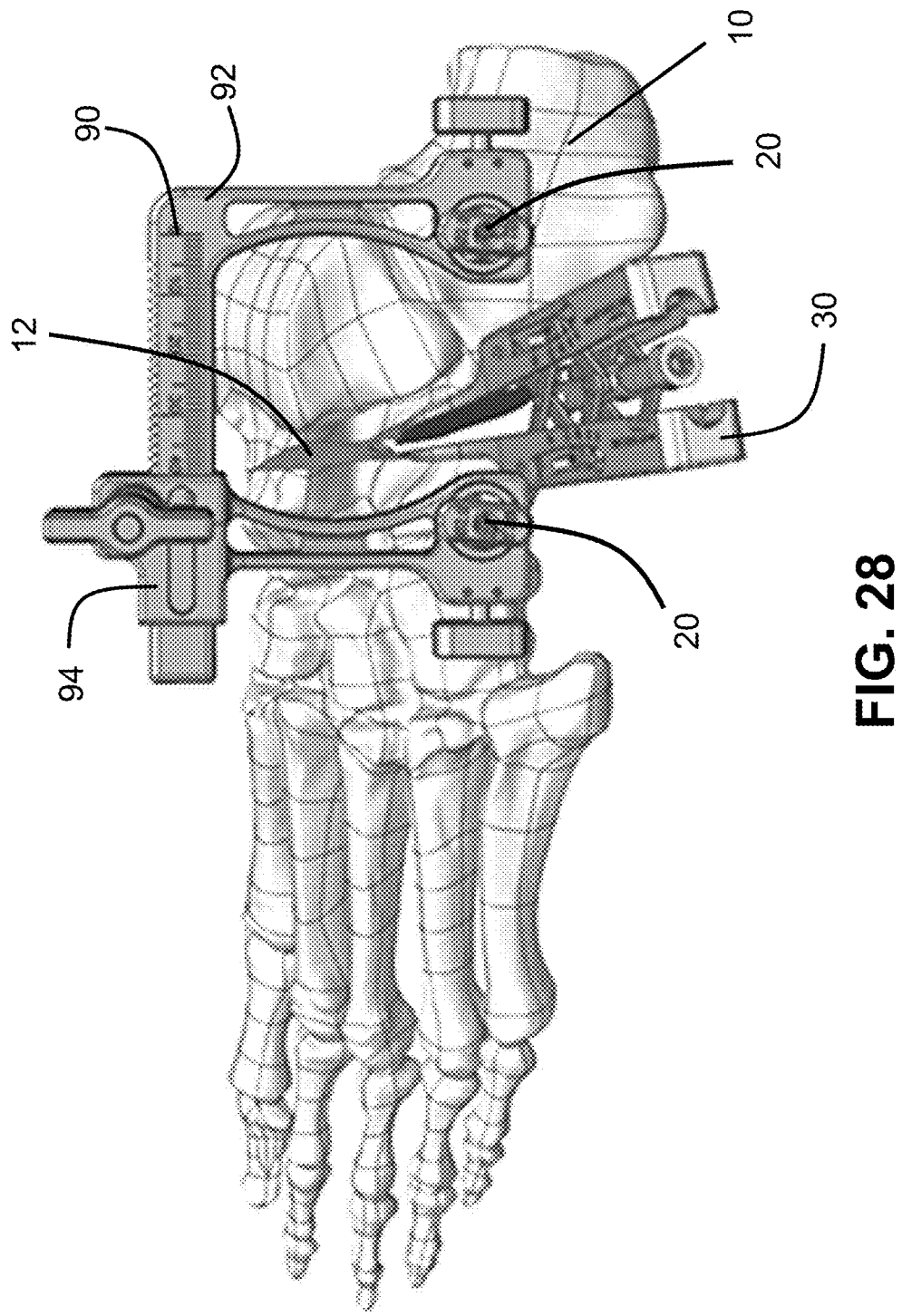
FIG. 28 shows a bridging apparatus attached to a foot, with a spreading device inserted into an incision.

Yet another embodiment of the present invention pertains to an adjustable bridging and distraction device 90, as seen in FIGS. 26, 27, and 28, and as described in FIGS. 15-28. Referring to FIGS. 15, 16, and 17, a subassembly 91 of bridging device 90 is shown. Subassembly 90 does not include collets 98, which will be discussed later with regards to FIGS. 18-20.

FIGS. 15, 16, and 17 show a subassembly 91 of a bridging device 90 that is adapted and configured to assist in separation, and to maintain separation, of two bones. Device 91 includes a rack assembly 92 and a pinion assembly 94 that are adjustably movable relative to one another, and further lockable in a position relative to one another.

It can be seen that rack assembly 92 includes a rack gear 92b located along a portion of a pinion guide 92d. An arm extends from the rack gear 92b, and provides pivotal support for a variable angle post assembly 96. Pinion assembly 94 includes a rack receptacle 94d and rotatable pinion gear 94b. An arm 94a extends from rack receptacle 94d, and supports at one end a variable angle post assembly 96.

Although what has been shown and described are a pair of identical variable angled post assemblies 96 located at the end of their respective arms, it is understood that the post structures can also be fixed in position relative to the arm, and that the two posts assemblies need not be identical. In some embodiments, one of the post assemblies is pivotal in two orthogonal directions (as will be described later), or pivotal in only a single direction, or fixed.

Referring briefly to FIG. 26, the bridging and distraction device 90 differs from subassembly 91, in that each of the arms 92a and 94a include a corresponding bone attachment assembly 92c and 94c, respectively. Now referring to FIG. 18, a cross sectional view of a representative bone attachment assembly 92c is shown. As discussed above, it is understood that in some embodiments the bone attachment assemblies 92c and 94c are identical, and this discussion of assembly 92c applies as well to assembly 94c.

It can be seen that the arm 92a includes a generally spherical pocket 92f that supports within it the generally spherical head 96b of post assembly 96. A generally cylindrical post 96a extends from one side of the spherical shape, and defines an internal lumen 96a having a larger inner diameter toward the sphere 96b, and a smaller inner diameter toward the bone contact surface 96f.

Figures 18, 19, 20:
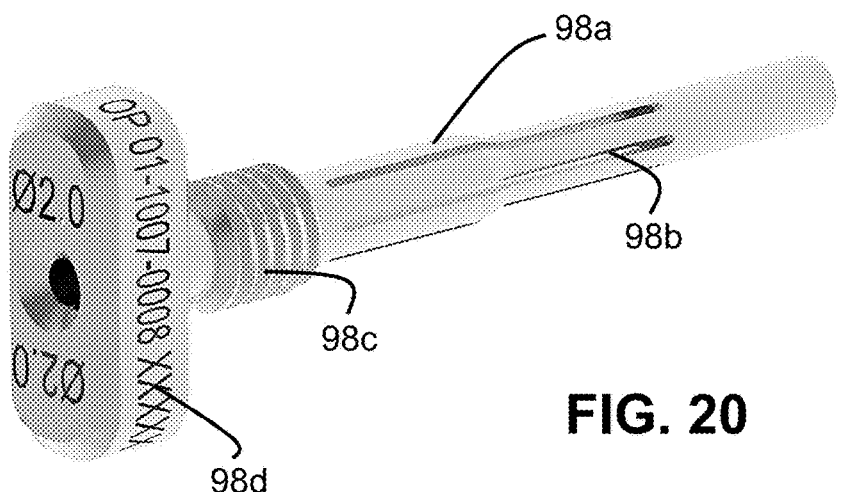
FIG. 18 is CAD line drawing of a side elevational cross sectional assembly of a bone attachment assembly according to one embodiment of the present invention.
FIG. 19 is a side elevational view of a portion of the apparatus of FIG. 18.
FIG. 20 is a perspective CAD surface representation of the apparatus of FIG. 19.

Located within the lumen 96e is a collet 98 or guide wire receptacle that includes threads 98c for threaded coupling to the entrance of lumen 96e. Collet 98 further includes a shaft 98a that extends in a direction toward the distal opened end of post 96a. Referring to FIG. 20, it can be seen that the shaft 98a includes a larger outer diameter proximate to the threaded interface 98c, and a smaller outer diameter proximate to the distal end. Referring again to FIG. 18, it can be seen that these two outer diameters correspond to, and are adapted and configured to fit within, the larger and smaller inner diameters of lumen 96e.

FIGS. 19 and 20 further show a plurality of slots 98b that extend along an intermediate length of shaft 98a. These slots 98b produce a region of reduced hoop stiffness, such that compressive loading of shaft 98a within lumen 96e results in compression of the outer diameters of shaft 98a along the length of the reduced hoop stiffness. This compression in turn results in compression of the inner diameter in lumen 98e of collet 98. Referring to FIG. 18, it can be seen that when a guidewire 20 is inserted within lumen 98e, that threaded coupling of the collet into the post will result in compression of post 96a against shaft 98a, especially as the length of the shaft 98 that transitions (from the larger O.D. to the smaller O.D.) is placed into tight and compressing contact with the transitional region (from larger I.D. to smaller I.D.) of post 96a. After sufficient tightening of the threaded coupling 98c, the wire 20 is held in place by friction relative to collet 98, which is held in place by the threaded connection to head 96b.

Figures 21, 22:
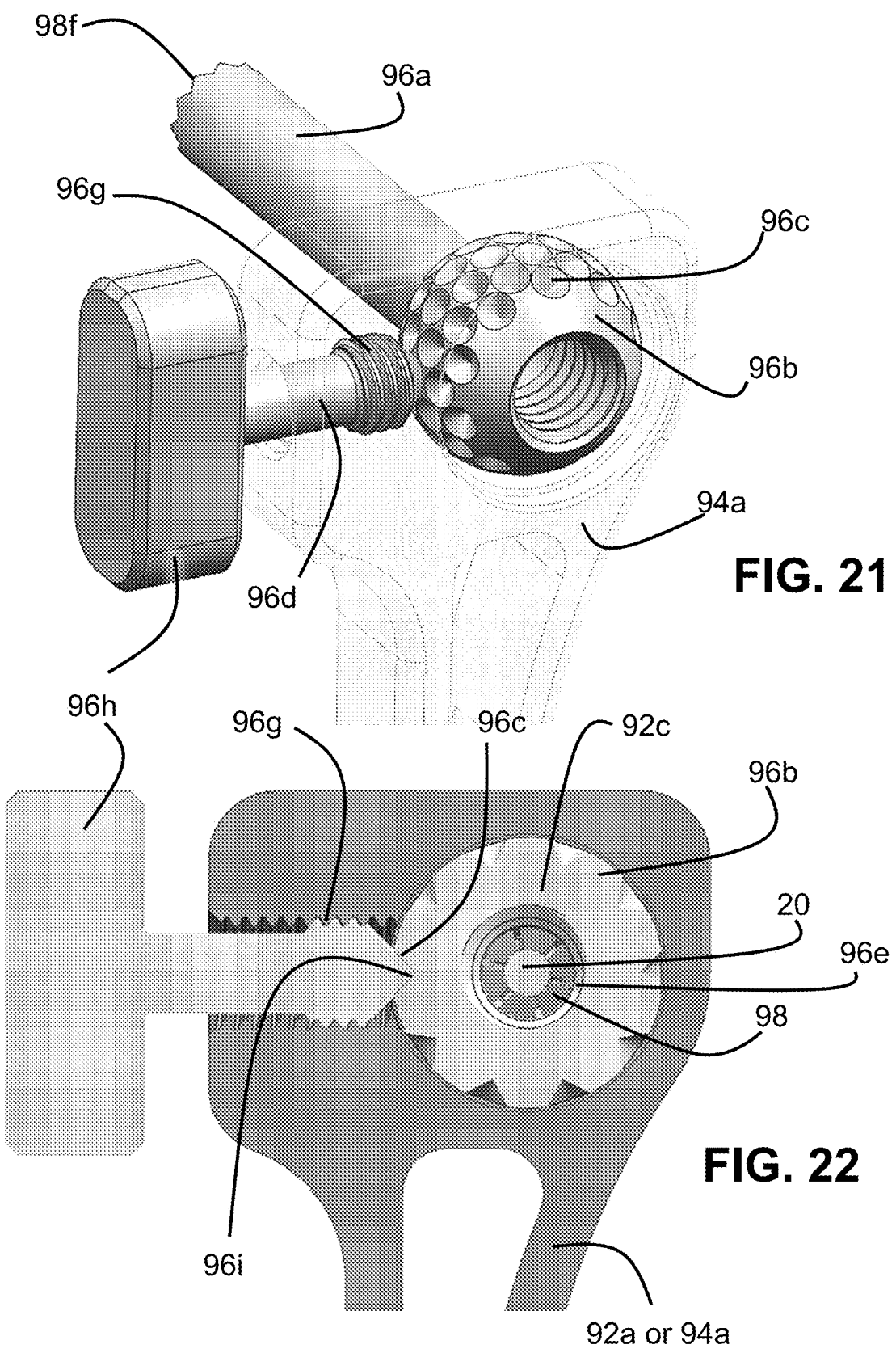
FIG. 21 is a CAD surface representation of a portion of the apparatus of FIG. 18.
FIG. 22 is a cross sectional representation of the apparatus of FIG. 18, as taken along line 22-22 of FIG. 18.
Figure 23:
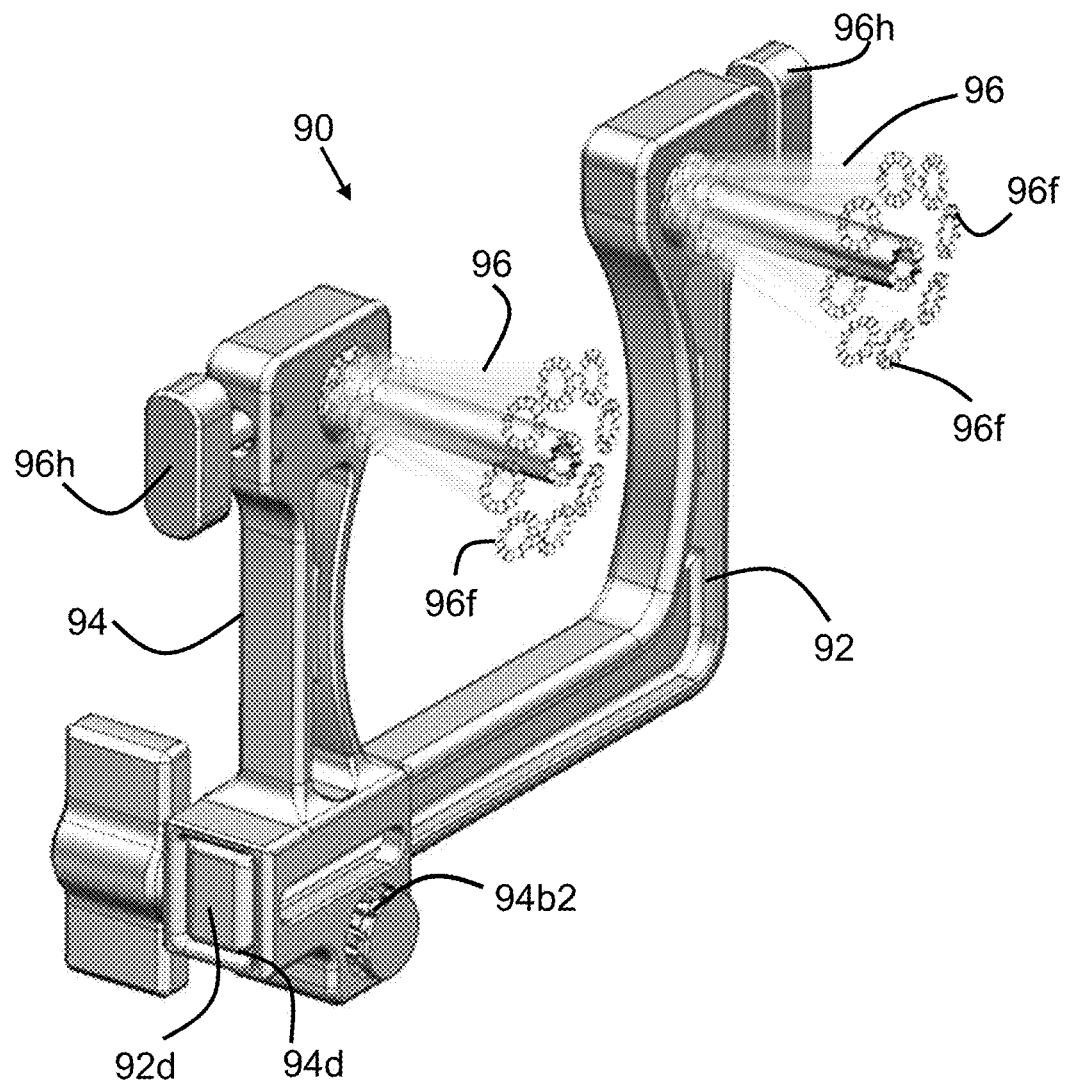
FIG. 23 is a perspective top, rear elevational view of the apparatus of FIG. 16, showing a variety of positions for the variable angle posts.

FIGS. 21, 22, and 23 depict the manner in which a bone attachment assembly 92c can pivot, and further be locked into a predetermined angular orientation. FIG. 21 shows a post assembly 96 and external locking device (96g, 96h, and 96i), both coupled to arm 94a (shown partially transparent). It can be seen that spherical head 96b preferably includes a plurality of recesses or dimples 96c extending around the periphery of the outer surface. In one embodiment, these recesses 96c are also preferably at a plurality of latitudes between the threaded interface of the head and the post 96a.

FIGS. 21 and 22 further show an adjustable external locking device that can be used to lock post assembly 96 into a predetermined angular orientation relative to arm 94a. The external locking device includes a projection 96i that can be received securely within a corresponding recess 96c. Once the correct angular orientation has been established, the physician can rotate knob 96h, this rotational movement being transformed into linear motion by the threaded coupling and driving projection 96i into a recess 96c.

Also shown in the cross section of FIG. 22 is the guidewire 20 within the lumen of collet 98. It can be seen that the lumen 96e has a centerline that intersects the center of spherical head 96b. However, in yet other embodiments the centerline of lumen 96e can be offset from the center of the sphere, such that rotation of shafts 96a and 96b will result in a limited third degree of lateral movement for wire 20 relative to arm 92a or 94a. Referring briefly to FIG. 23, it can be seen that the pattern of recesses 96e (as best seen in FIG. 21) result in the bone contact surface 96f (and likewise the guidewire 20) being able to move in two orthogonal pivotal directions.

Figures 24, 25A, 25B:
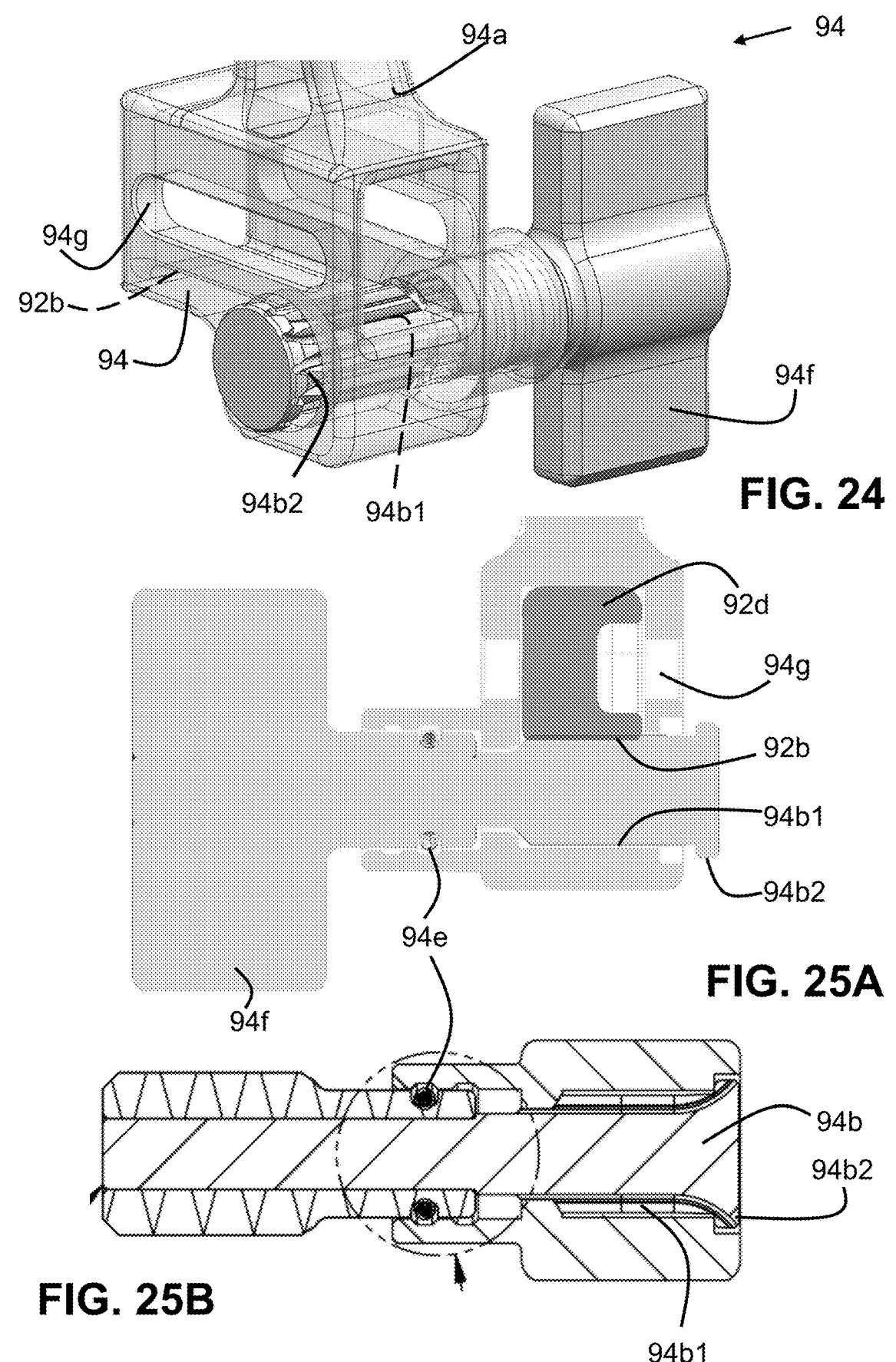
FIG. 24 is a perspective CAD representation, with some components shown partially transparent of a portion of the apparatus of FIG. 16.
FIG. 25A is a cutaway view of the apparatus of FIG. 24, as taken down the centerline, and shown with the rack and pinion being unlocked.
FIG. 25B is a cutaway view of a portion of the apparatus of FIG. 25A, as taken down the centerline, and shown with the rack and pinion being locked.

FIGS. 24, 25A, and 25B show various depictions of a portion of pinion assembly 94. Referring to FIG. 25A and briefly to FIGS. 17 and 23, it can be seen that the end of the rack includes a pivot guide 92d of rack assembly 92, and is received within a corresponding rack receptacle 94d of pinion assembly 94. As shown in FIG. 25, within this receptacle the conventional pinion teeth 94b1 engage with the rack gear teeth 92b. In a conventional manner, rotation of the pinion shaft results in translation of rack assembly 92. To adjust the rack position, the physician turns knob 94f by hand, until the lateral separation of the bone attachment assemblies 92c and 94c are appropriate. The configuration shown in FIG. 25A is used during adjustment of the rack position.

Once the proper position has been established, FIG. 25B shows a manner in which the rack and pinion are locked into a position. Referring briefly to FIG. 25A, it can be seen that a retention spring 94e (such as a ball seal spring made by Bal Seal™) is located within a distalmost groove of a shaft coupled to handle 94f, and also within a groove of a housing of pinion assembly 94.

It can be seen in FIG. 25A that pinion teeth 94b1 are engaged along the length of rack gear teeth 92b. After the relative positions of the bone attachment assemblies are appropriate, the physician can pull the pinion gear 94b (which is attached to handle 94f), moving the larger, rack-interfering teeth 92b2 of pinion gear 94b into the edge of the rack 92b. In so doing, the rack is no longer able to slide relative to the pinion assembly. In this gear-interfering position (as seen in FIG. 25B), it can be seen that the retention spring assembly 94e has moved with handle 94f, such that it is now located within the proximal-groove of the housing. This retention spring expands into this groove, and provides securement of the shaft in this pulled configuration. However, to release the rack from the pinion, the physician simply pushes on the handle 94f, causing the retention spring 94f to compress and move into the distalmost groove, which restores normal engagement to the rack gear and pinion gear.

FIGS. 26 and 27 show attachment and subsequent adjustment of a bridging and distraction device 90. Referring to FIG. 26, it can be seen that guide wires 20 have been located in the proper position in two separable bone segments 10. Referring to FIG. 27, it can be seen that the handle 94f has been rotated, such that the engaged rack and pinion gears have moved arm 92a relative to arm 94a.

FIG. 28 further shows a bridging and distraction device 90 attached to bones 10 of a foot. The incision 12 has previously been made, and a spreading device 30 is used to open the incision. The guide wires 20 are each residing within a corresponding hole within a bone 10, and the two wires 20 (located within corresponding bone attachment assemblies 92c and 94c) have been spread apart by operation of the rack assembly 92 and pinion assembly 94 to achieve a desired spacing. It can be seen in FIGS. 26 and 27 that a measurement indicia 92e on rack assembly 92 can be viewed within a window 94g of pinion assembly 94.

With regards to device 90 as shown in FIG. 26, 27, or 28, the instructions for use are as follows:

1. Insert desired collets (1.6 mm or 2.0 mm) into the arms of the Articulating Compressor/Distractor.

2. Ensure the rack & pinion knob is in the 'unlocked' position. If it is not, push in the knob to unlock it.
3. Unlock spherical joints of arms by loosening the arm knobs on either side.
4. Insert appropriate wires into the bone on either side of osteotomy. Ensure enough space is between the wires for the planned osteotomy as well as for desired final fixation (plate, screws, etc.).
5. Slide tubes of the Articulating Compressor/Distractor over the wires.
6. Lock spherical joints into desired orientation by tightening the arm knobs on either side.
7. Lock collets onto wires. Spherical joints/arm knobs must be locked to lock collets onto wire.
8. If desired, unlock spherical joints by loosening the arm knobs.
9. Turn rack & pinion knob to compress/distract the bone fragments. Turning the knob to the right will distract the fragments. Turning the knob to the left will compress the fragments.
10. Once desired correction is achieved and confirmed via fluoroscopy, pull the rack & pinion knob towards you until you hear a click to lock the rack & pinion in place. This will hold the osteotomy until final fixation is applied.
11. After final fixation is achieved, unlock collets and remove device. Arm knobs may be loosened after loosening the collets to aid in removal of the device.
12. Remove guide wires.

Various aspects of different embodiments of the present invention are expressed in paragraphs X1, X2, X3, X4, and X5 as follows:

X1. One aspect of the present invention pertains to a kit for performing an osteotomy. The kit preferably includes a spreading device, a bone plate, and a bridge.

X2. Another aspect of the present invention pertains to a device for an osteotomy. The device preferably includes a bridge having a peripheral wall that surrounds an open interior. The device preferably includes a plurality of standoffs adapted and configured for contact with a bone and for supporting the peripheral wall, each standoff supporting the peripheral wall elevated above the bone surface.

X3. Yet another aspect of the present invention pertains to a device for being inserted into material and spreading the material open. The device preferably includes a device adapted and configured to spread apart the material, the device including a pair of members adapted and configured to contact the material and a spreading mechanism coupled to each member, the device having a fully nested position and a range of opened positions. The device preferably includes each of the pair of members having an outer surface with a gripping region adapted and configured for being gripped by a hand. In the fully nested position the spreading mechanism is contained between the gripping regions of the pair of members.

X4. Still another aspect of the present invention pertains to a device for bone surgery. The device preferably includes a first frame having an arm and a rack gear, the first arm including a first pivotal collet adapted and configured for securement to a guide wire; and a second frame having an arm and a rotatable pinion gear, the second arm including a second pivotal collet adapted and configured for securement to a guide wire; wherein the rack gear intermeshes with the pinion gear, the pinion gear including a knob for manual rotation, one of the first frame or the second frame including a gear train lock.

X5. Yet another aspect of the present invention pertains to a device for bone surgery. The device preferably includes a frame having a pair of spaced apart arms; each arm supporting a corresponding standoff post, each standoff post including a head and a body, the head being pivotally captured by the arm and pivotal relative to the arm in two orthogonal directions, the body and head defining a bore therethrough, each arm including a corresponding external locking device for locking the pivotal orientation of the head relative to the arm.

Yet other embodiments pertain to any of the previous statements X1, X2, X3, X4, or X5, which are combined with one or more of the following other aspects. It is also understood that any of the aforementioned X paragraphs include listings of individual features that can be combined with individual features of other X paragraphs.

Wherein the peripheral wall includes an opening.

Wherein there are only two posts connected by a wall in a generally straight line.

Wherein there are only two posts and the wall is generally U-shaped.

Wherein spreading mechanism including a threaded actuator, wherein rotation of the threaded actuator results in displacement of one member relative to the other member throughout the range of opened positions.

Wherein the bridge attaches to said bone at a location different than the attachment of the bone plate.

Wherein attachment posts are located on opposite sides of the opening.

Wherein each attachment post includes a through hole adapted and configured to accept means for aligning said bridge to the bone.

Wherein an end of each attachment post includes a surface profile that penetrates into the bone surface.

Wherein said bone plate has a wider section having a first width and a narrower section having a second width, and one pair of attachment posts are spaced apart to accommodate therebetween the second width and another pair of attachment posts are spaced apart to accommodate therebetween the first width.

Wherein said bridge including at least one handle; wherein said handle extends from the bridge in a direction outward from the bone surface; wherein said bridge includes a pair of handles on opposite sides of the open interior.

Wherein said bridge includes at least three standoffs, each said standoff being spaced apart from each other standoff along the length of the peripheral wall.

Wherein the opening in the peripheral wall is between two adjacent standoffs.

Wherein at least four standoffs, each said standoff being spaced apart from each other standoff along the length of the peripheral wall; wherein no three of the four standoffs combine to define a right angle.

Wherein the opening in the peripheral wall is between two adjacent standoffs.

Wherein the standoffs are separated from one another such that at least one standoff is located on opposite sides of an expanded incision in a bone.

Wherein the bores are angled to generally intersect with the center of the bone.

Which further comprises a plurality of guide wires each adapted and configured to fit within a respective bore and extend into the bone.

Which further comprises a plurality of fasteners each adapted and configured to fit within a respective bore and extend into threaded engagement with a corresponding hole in the bone.

Wherein said peripheral wall includes two opposite sides and a third side interconnecting the two opposite sides, and the opening is opposite of the third side.

Wherein said peripheral wall includes opposite, interconnected sides, at least one of said standoffs being located on one side of the peripheral wall and another said standoff being located on the other opposite side of said peripheral wall.

Wherein said posts are the only contacts of said bridge with the surface of the bone.

Wherein each said bore is not parallel to any other of said bores.

Wherein the peripheral wall has an underside spaced apart from the bone surface by the standoffs, and the underside and the volume between the underside and the bone surface is largely open.

Wherein in the fully nested position the proximal-most ends of the pair of members coact to form an end region adapted and configured to accept hammering impacts.

Wherein in an opened position intermediate of the fully nested position and the fully opened position the distal-most ends of the pair of member remain proximate to one another and the pair of members are arranged in a V shape.

Wherein in throughout the range of opened positions the distal-most ends of the pair of members remain substantially proximate each other.

Wherein in throughout the range of opened positions the distal-most ends of the pair of members remain spread apart less than the proximal-most end of the pair of members; wherein the proximal ends are not hinged to one another.

Wherein the bone contact regions have a shape that tapers along the axis from a greater height proximate to the gripping region to a less height at the distal-most end.

Wherein in the fully opened position said spreading mechanism is contained between the gripping regions of the pair of members.

Wherein rotation of said threaded member results in angular and/or linear displacement of one member relative to the other member throughout the range of opened positions.

Wherein the members each include opposing lateral sides and the fully nested spreading mechanism is contained between the lateral sides.

Wherein said device has a longitudinal axis, and the threaded actuator is axially aligned.

Wherein the gripping region of each of the pair of members includes opposing lateral surfaces, the lateral surfaces and the outer surface defining an interior volume, and in the fully nested position said spreading mechanism is contained within the volume.

Wherein actuation of said gear train lock results in said rack gear interfering with said pinion gear.

Wherein said gear train lock includes a section of said pinion gear having a major diameter that interferes with said rack gear.

Wherein said knob is attached to said pinion gear, and said knob and said gear can be moved to different positions relative to said rack gear.

Wherein said first frame includes a first locking device for locking the pivotal orientation of said first collet, and said second frame includes a second locking device for locking the pivotal orientation of second first collet.

Wherein said first pivotal collet is pivotal in two orthogonal directions, and said second pivotal collet is pivotal in two orthogonal directions.

Wherein said arms are spaced apart sufficiently to receive therebetween a device for spreading apart an incision in a bone.

Wherein the head is generally spherical, and the arm includes a generally spherical pocket for capturing therein the head.

Wherein the head includes a plurality of dimples, and said external locking device includes a projection receivable within a dimple for locking the position of the head relative to the arm.

Wherein the bore includes internal threads, and which further comprises a collet having a shaft including external threads for threaded coupling to the bore, said collet including a lumen within the shaft adapted and configured for frictional coupling to a guide wire.

Which further comprises a collet having a shaft defining a lumen and receivable within the bore, the bore including a region of reduced inner diameter, the shaft having a length of reduced hoop stiffness, wherein insertion of the length within the region reduces the cross sectional area of the lumen.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A device for surgery on a bone, comprising:
   a bridge having a peripheral wall that surrounds an open interior, the peripheral wall including a first peripheral wall surface portion, the first peripheral wall surface portion being arranged to face the open interior without facing the bone; and
   a plurality of standoffs, each of the standoffs having one end adapted and configured for contact with the bone and an opposite end supporting said peripheral wall, each of the standoffs being arranged to space the peripheral wall apart from the bone such that the open interior is elevated above the bone; and
   a plurality of elongated through bores, each of the elongated through bores extending from a respective one of the one ends to the corresponding opposite end and through the peripheral wall,
   wherein said peripheral wall includes an opening located between at least two standoffs.

2. The device of claim 1, wherein the bridge includes at least one handle.

3. The device of claim 2, wherein the handle is arranged to extend from the peripheral wall in a direction outward from the bone surface.

4. The device of claim 2, wherein the bridge includes a pair of handles on opposite sides of the open interior.

5. The device of claim 1, wherein the plurality of standoffs includes at least three standoffs, each of the at least three standoffs being spaced apart from each other of the three standoffs along a length of the peripheral wall.

6. The device of claim 5, wherein the opening in the peripheral wall is between two adjacent standoffs.

7. The device of claim 1, wherein the plurality of standoffs includes at least four standoffs, each of the at least four standoffs being spaced apart from each other of the at least four standoffs along a length of the peripheral wall.

8. The device of claim 1, wherein the plurality of standoffs includes at least two standoffs, each of the at least two standoffs being spaced apart from the other of the at least two standoffs along a length of the peripheral wall.

9. The device of claim 1, wherein the plurality of standoffs includes at least two standoffs, the peripheral wall interconnects the at least two standoffs, and the peripheral wall is generally U-shaped.

10. The device of claim 1, wherein at least two of the standoffs are separated from one another such that they are arranged to be located on opposite sides of an expanded incision in the bone.

11. The device of claim 10, wherein each of the standoffs has a respective centerline, and the centerlines are arranged such that no two of the centerlines intersect.

12. The device of claim 1, further comprising:
   a plurality of guide wires,
   wherein a respective one of each of the guide wires is adapted and configured to fit within a respective one of the elongated through bores and extend into a corresponding hole in the bone.

13. The device of claim 1, further comprising:
   a plurality of fasteners,
   wherein each of the fasteners is adapted and configured to fit within a respective one of the elongated through bores and extend into threaded engagement with a corresponding hole in the bone.

14. The device of claim 1, wherein the peripheral wall includes two opposite sides and a third side interconnecting the two opposite sides, and the opening is opposite of the third side.

15. The device of claim 1, wherein the peripheral wall includes opposite, interconnected sides, at least one of the standoffs is located on one side of the peripheral wall, and another of the standoffs is located on the other opposite side of the peripheral wall.

16. The device of claim 1, wherein the standoffs include posts arranged to be the only contacts of said bridge with the bone.

17. The device of claim 1, wherein no one of the elongated bores is parallel to any other one of the elongated bores.

18. The device of claim 1, wherein the peripheral wall has an underside spaced apart from the bone by the standoffs, and a volume between the underside and the bone is largely open.

* * * * *